United States Patent
Nakazato et al.

(10) Patent No.: US 11,435,354 B2
(45) Date of Patent: Sep. 6, 2022

(54) ADENOCARCINOMA DETECTION METHOD

(71) Applicants: University of Miyazaki, Miyazaki (JP); Osaka University, Osaka (JP)

(72) Inventors: Masamitsu Nakazato, Miyazaki (JP); Nobuhiro Matsumoto, Miyazaki (JP); Yasuji Arimura, Miyazaki (JP); Hironobu Tsubouchi, Miyazaki (JP); Toshifumi Takao, Osaka (JP); Nobuaki Okumura, Osaka (JP); Masafumi Fukuda, Osaka (JP)

(73) Assignees: UNIVERSITY OF MIYAZAKI, Miyazaki (JP); OSAKA UNIVERSITY, Osaka (JP)

( * ) Notice: Subject to any disclaimer, the term of this patent is extended or adjusted under 35 U.S.C. 154(b) by 384 days.

(21) Appl. No.: 15/999,477

(22) PCT Filed: Feb. 16, 2017

(86) PCT No.: PCT/JP2017/005729
§ 371 (c)(1),
(2) Date: Aug. 17, 2018

(87) PCT Pub. No.: WO2017/142025
PCT Pub. Date: Aug. 24, 2017

(65) Prior Publication Data
US 2020/0333343 A1 Oct. 22, 2020

(30) Foreign Application Priority Data
Feb. 19, 2016 (JP) ............................. JP2016-030267

(51) Int. Cl.
*G01N 33/574* (2006.01)
*C07K 14/705* (2006.01)
*C07K 14/78* (2006.01)
*G01N 33/68* (2006.01)

(52) U.S. Cl.
CPC ..... *G01N 33/57423* (2013.01); *C07K 14/705* (2013.01); *C07K 14/78* (2013.01); *G01N 33/6803* (2013.01)

(58) Field of Classification Search
CPC ......... G01N 33/57423; G01N 33/6803; C07K 14/705; C07K 14/78
See application file for complete search history.

(56) References Cited

U.S. PATENT DOCUMENTS

2015/0353629 A1* 12/2015 Hellstrom .............. C07K 16/18
530/387.9

FOREIGN PATENT DOCUMENTS

| JP | 2006-284389 A | 10/2006 |
| JP | 2006-308533 A | 11/2006 |
| JP | 2007-536206 A | 12/2007 |
| JP | 2010-528265 A | 8/2010 |
| JP | 2012-526976 A | 11/2012 |
| JP | 2014-025868 A | 2/2014 |
| JP | 2014-115186 A | 6/2014 |
| WO | WO-2005-040222 | 5/2005 |
| WO | WO-2008-144034 A1 | 11/2008 |
| WO | WO-2010061393 A1 * | 6/2010 ............. C07K 16/38 |
| WO | WO-2010-130839 A1 | 11/2010 |

OTHER PUBLICATIONS

Bingle et al., The putative ovarian tumour marker gene HE4 (WFDC2), is expressed in normal tissues and undergoes complex alternative splicing to yield multiple protein isoforms, Oncogene, 21, 2768-2773 (Year: 2002).*
Yamashita et al., Prognostic significance of HE4 expression in pulmonary adenocarcinoma, Tumor Biol. 32:265-271, Publication Date: Oct. 15, 2010 (Year: 2010).*
Atagi et al., "Thoracic radiotherapy with or without daily low-dose carboplatin in elderly patients with non-small-cell lung cancer: a randomised, controlled, phase 3 trial by the Japan Clinical Oncology Group (JCOG0301)", The Lancet Oncology, Jul. 1, 2012, vol. 13, Issue 7, pp. 671-678.
Matsuoka et al., "Prognostic value of carcinoembryonic antigen and CYFRA21-1 in patients with pathological stage I non-small cell lung cancer", European Journal of Cardio-thoracic Surgery, 32 (2007), pp. 435-439.
Molina et al., "Assessment of a Combined Panel of Six Serum Tumor Markers for Lung Cancer", Am J Respir Crit Care Med, Feb. 15, 2016, vol. 193, Iss 4, pp. 427-437.
Sawabata et al., "Japanese Lung Cancer Registry Study of 11,663 Surgical Cases in 2004: Demographic and Prognosis Changes Over Decade", Journal of Thoracic Oncology, vol. 6, No. 7, Jul. 2011, pp. 1229-1235.
Scagliotti et al., "Phase III Study Comparing Cisplatin Plus Gemcitabine With Cisplatin Plus Pemetrexed in Chemotherapy-Naive Patients With Advanced-Stage Non-Small-Cell Lung Cancer", Journal of Clinical Oncology, Jul. 20, 2008, vol. 26, No. 21, pp. 3543-3551.

(Continued)

*Primary Examiner* — Peter J Reddig
*Assistant Examiner* — Cheng Lu
(74) *Attorney, Agent, or Firm* — Foley & Lardner LLP

(57) ABSTRACT

There is provided a simple and minimally invasive adenocarcinoma detection method. The adenocarcinoma detection method of the present invention includes a step of detecting in vitro a presence or absence of an abnormal cleavage in a specific protein in a test subject-derived sample. The abnormal cleavage in the specific protein is, for example, a cleavage resulting in one or more breaks in a peptide bond in the specific protein and/or a cleavage resulting in a deletion of one or two more amino acid residues at one or more sites of the specific protein. The adenocarcinoma detection method of the present invention includes a step of detecting a presence or amount of a protein having the abnormal cleavage or a decrease in an amount of a normal protein.

6 Claims, 10 Drawing Sheets

Specification includes a Sequence Listing.

(56) References Cited

OTHER PUBLICATIONS

Kimura, N. et al. (1998) "Molecular Identification of the Antigens Recognized by Monoclonal Antibody JT95 Specific for Thyroid Carcinomas," Biochemical and Biophysical Research Communications 251(2):449-453.

International Search Report (ISA/JP) for International Application No. PCT/JP2017/005729, dated May 23, 2017.

English Translation of International Preliminary Report on Patentability (ISA/JP) for International Application No. PCT/JP2017/005729, dated Aug. 23, 2018.

* cited by examiner

ADENOCARCINOMA DETECTION METHOD

CROSS-REFERENCE TO RELATED APPLICATIONS

This application is a national stage entry under 35 U.S.C. § 371 of International Application No. PCT/JP2017/005729, filed Feb. 16, 2017, which claims priority to Japanese Application No. 2016-030267, filed Feb. 19, 2016, the content of each of which is incorporated by reference in its entirety.

SEQUENCE LISTING

The instant application contains a Sequence Listing which has been submitted electronically in ASCII format and is hereby incorporated by reference in its entirety. Said ASCII copy, created on Jun. 8, 2020, is named 104788-0320_SL-2.txt and is 51,647 bytes in size.

TECHNICAL FIELD

The present invention relates to an adenocarcinoma detection method.

BACKGROUND ART

The adenocarcinoma is one of epithelial malignant tumors arising from cells in the secretory gland tissue. Lung adenocarcinoma, liver adenocarcinoma, pancreatic adenocarcinoma, lymphatic adenocarcinoma, uterine adenocarcinoma, seminal adenocarcinoma, gastric adenocarcinoma or the like can occur in all organs of the body.

Among them, the lung adenocarcinoma is one of adenocarcinomata of which initial symptom is unlikely to appear and of which early detection is difficult. Among lung cancer tissue types, lung adenocarcinoma most frequently occurs. Of patients with lung cancer, male patients with lung adenocarcinoma account for about 40%, female patients with lung adenocarcinoma account for about 70%, and the whole patients with lung adenocarcinoma account for about 50%. Since lung cancer is number one in the number of malignant tumor deaths in Japan, there is a need for a technique to detect lung adenocarcinoma in an early stage.

The survival rate for patients with lung cancer decreases with the progress of clinical stage. For example, in patients with non-small cell lung cancer in operable clinical stages IA, IB, IIA, IIB, and IIIA, the 5-year survival rates are 82.0%, 66.1%, 54.5%, 46.1%, and 42.8% (Non-Patent Document 1). The median survival times of patients with non-small cell lung cancer in inoperable clinical stages IIIB and IV are 22.4 months (Non-Patent Document 2) and 10.3 months (Non-Patent Document 3), respectively.

Serum carcinoembryonic antigen (CEA) is used for clinical diagnosis as an existing tumor marker for lung adenocarcinoma. However, the positive rate of CEA in cases with lung adenocarcinoma is only 36.6 to 56.5% (Non-Patent Documents 4 and 5), and the positive rate of lung adenocarcinoma in early stage, particularly in stage I, is as low as 27% (Non-Patent Document 5). In the case of CEA, it is difficult to diagnose lung adenocarcinoma in a fundamentally treatable stage.

Examples of tumor markers to be developed for clinical application include serum CYBP (Patent Document 1) and UBE2L3 (Patent Document 2). However, these markers are subjected to the conditions where blood is collected from patients, and thus are invasive. Such examination is required to be minimally invasive.

PRIOR ART DOCUMENTS

Patent Document

Patent Document 1: JP-W-2012-526976
Patent Document 2: JP-A-2014-115186

Non-Patent Document

Non-Patent Document 1: Sawabata N, et al., J Thorac Oncol. 6: 1229-35, 2011.
Non-Patent Document 2: Atagi S, et al., Lancet Oncol. 13: 671-8, 2012.
Non-Patent Document 3: Scagliotti G V, et al., J Clin Oncol. 26: 3543-51, 2008.
Non-Patent Document 4: Molina R, et al., Am J Respir Crit Care Med, 2015 Oct. 14. [Epub ahead of print]
Non-Patent Document 5: Matsuoka K, et al., Eur J Cardiothorac Surg. 32: 435-9, 2007.

SUMMARY OF THE INVENTION

Problems to be Solved by the Invention

The present invention aims to provide an adenocarcinoma detection method.

Means for Solving the Problems

The present inventors have found an increase in fragmentation of amino acids of specific proteins in body fluids and a decrease in proteins having a normal structure, and exposed parts due to breaks at abnormal positions of proteins or due to deletion of intermediate positions, which are seen specifically in adenocarcinoma patients. As a result of diligent studies to establish an adenocarcinoma detection method which is simple, minimally invasive or non-invasive, they have completed the present invention.

That is, the present invention provides the following [1] to [11].

[1] An adenocarcinoma detection method comprising a step of detecting in vitro a presence or absence of an abnormal cleavage in one or two or more specific proteins in a test subject-derived sample, wherein the specific protein is derived from any one of the proteins selected from the group consisting of the following (i) to (x):
(i) α-1-antitrypsin
(ii) α-1-microglobulin/bikunin precursor
(iii) CD59
(iv) Fibronectin
(v) Lectin, Mannose-Binding 2
(vi) Vasorin
(vii) WAP four-disulfide core domain protein 2
(viii) Membrane-bound carboxypeptidase M
(ix) Deoxyribonuclease-1; and
(x) WNT1-inducible-signaling pathway protein 2.
[2] The adenocarcinoma detection method according to [1], wherein the abnormal cleavage in the specific protein is a cleavage resulting in one or more breaks in a peptide bond and/or a cleavage resulting in a deletion of one or two or more amino acid residues at one or more sites of the specific protein.

[3] The adenocarcinoma detection method according to [1] or [2], wherein the step of detecting in vitro the presence or absence of the abnormal cleavage in the one or two or more specific proteins in the test subject-derived sample includes at least one selected from the group consisting of the following (1) to (4):

(1) detecting a decrease in a relative amount of a protein having a normal structure in the specific protein in the test subject-derived sample;

(2) detecting a presence or an increase in a relative amount of a protein having a deletion of an amino acid residue on a C-terminal side of the specific protein in the test subject-derived sample;

(3) detecting a presence or an increase in a relative amount of a protein having a deletion of an amino acid residue on an N-terminal side of the specific protein in the test subject-derived sample; and (4) detecting a presence or an increase in a relative amount of a protein having a break or deletion in any intermediate site of an amino acid sequence of the specific protein in the test subject-derived sample.

[4] The adenocarcinoma detection method according to [1], wherein the step of detecting in vitro the presence or absence of the abnormal cleavage in the specific protein in the test subject-derived sample includes detecting an amount or presence of at least one kind selected from the group consisting of the following (a) to (y):

(a) a protein fragment having a C-terminal amino acid sequence of GTEAAGAMF, SEQ ID NO: 11;

(b) a protein fragment having a C-terminal amino acid sequence of CVLFPYGG, SEQ ID NO: 12;

(c) a protein fragment having a C-terminal amino acid sequence of EYCGVPG, SEQ ID NO: 13;

(d) a protein fragment having a C-terminal amino acid sequence of EYCGVPGDG, SEQ ID NO: 14;

(e) a protein fragment having a C-terminal amino acid sequence of EYCGVPGDGDE, SEQ ID NO: 15;

(f) a protein fragment having a C-terminal amino acid sequence of EYCGVPGDGDEE, SEQ ID NO: 16;

(g) a protein fragment having a C-terminal amino acid sequence of EYCGVPGDGDEEL, SEQ ID NO: 17;

(h) a protein fragment having a C-terminal amino acid sequence of EYCGVPGDGDEELL, SEQ ID NO: 18;

(i) a protein fragment having a C-terminal amino acid sequence of GECVPGEQEPEP, SEQ ID NO: 19;

(j) a protein fragment having a C-terminal amino acid sequence of GECVPGEQEPEPILIP, SEQ ID NO: 20;

(k) a protein fragment having a C-terminal amino acid sequence of DLCNFNEQL, SEQ ID NO: 21;

(n) a protein fragment having a C-terminal amino acid sequence of FGFCPMA, SEQ ID NO: 22;

(p) a protein fragment having a C-terminal amino acid sequence of EGSCPQVNINFPQLG, SEQ ID NO: 23;

(q) a protein fragment having a C-terminal amino acid sequence of LPTGYY, SEQ ID NO: 24;

(r) a protein fragment having a C-terminal amino acid sequence of YLQGSSVQL, SEQ ID NO: 25;

(s) a protein fragment having a C-terminal amino acid sequence of EGSCPQVNIN, SEQ ID NO: 26;

(t) a protein fragment having a C-terminal amino acid sequence of ENYNQYDLN, SEQ ID NO: 27;

(u) a protein fragment having a C-terminal amino acid sequence of GAVVPDSALPFNFQAAY, SEQ ID NO: 28;

(v) a protein fragment having a C-terminal amino acid sequence of EGSCPQVNINFPQLGL, SEQ ID NO: 29;

(w) a protein fragment having a C-terminal amino acid sequence of GALCLLAEDDS, SEQ ID NO: 30;

(x) a protein fragment having a C-terminal amino acid sequence of EYCGVPGD, SEQ ID NO: 31; and (y) a protein fragment having a C-terminal amino acid sequence of GECVPGEQEPE, SEQ ID NO: 32.

[5] The adenocarcinoma detection method according to any one of [1] to [4], wherein the one or two or more specific proteins contain at least (ii) α-1-microglobulin/bikunin precursor, and the step of detecting in vitro the presence or absence of the abnormal cleavage includes detecting a decrease in a relative amount of a protein having a normal structure which is derived from α-1-microglobulin/bikunin precursor present in a test subject sample, and/or an amount or presence of a protein fragment derived from α-1-microglobulin/bikunin precursor.

[6] The adenocarcinoma detection method according to any one of [1] to [5], wherein the one or two or more specific proteins include at least (vii) WAP four-disulfide core domain protein 2, and the step of detecting in vitro the presence or absence of the abnormal cleavage includes detecting a cleavage of a peptide bond in any of the amino acid sequences at positions 80 to 93 of SEQ ID NO: 7 in the sequence listing, or a deletion of an amino acid residues around a cleavage site in any of the amino acid sequences at positions 80 to 93 of SEQ ID NO: 7.

[7] The adenocarcinoma detection method according to any one of [1] to [6], wherein the adenocarcinoma is lung adenocarcinoma.

[8] The adenocarcinoma detection method according to any one of [1] to [7], wherein the test subject-derived sample is urine.

[9] The adenocarcinoma detection method according to any one of [1] to [8], further comprising a step of using at least one method selected from the group consisting of a mass spectrometry measurement method, an immunochemical measurement method, and a chromatography method.

[10] The adenocarcinoma detection method according to [1], wherein the presence or absence of the abnormal cleavage in the specific protein is determined by a fragmentation rate of the specific protein, and the fragmentation rate is a value expressed by $$\text{protein fragmentation rate } (F_n) = C_n/I_n,$$

in which $C_n$ is an amount of each specific protein fragment, and $I_n$ is an amount of original protein derived from each specific protein fragment.

[11] The adenocarcinoma detection method according to [1], wherein the presence or absence of the abnormal cleavage in the specific protein is determined by a relative ratio of the fragmentation rate of the specific protein derived from the test subject and the fragmentation rate of a protein from a healthy individual, the relative ratio being expressed by $$\text{relative ratio } (R_n) \text{ of protein fragmentation rates between patient and healthy individual} = F_p/F_h,$$

in which $F_p$ is a protein fragmentation rate in patient sample, and $F_h$ is an average value of protein fragmentation rates of healthy individual group, and the abnormal cleavage is judged to be present when the relative ratio is greater than 1.

Effect of the Invention

According to the present invention, adenocarcinoma can be detected by a minimally invasive method using body fluids such as urine and blood.

MODE FOR CARRYING OUT THE INVENTION

Figure 1:
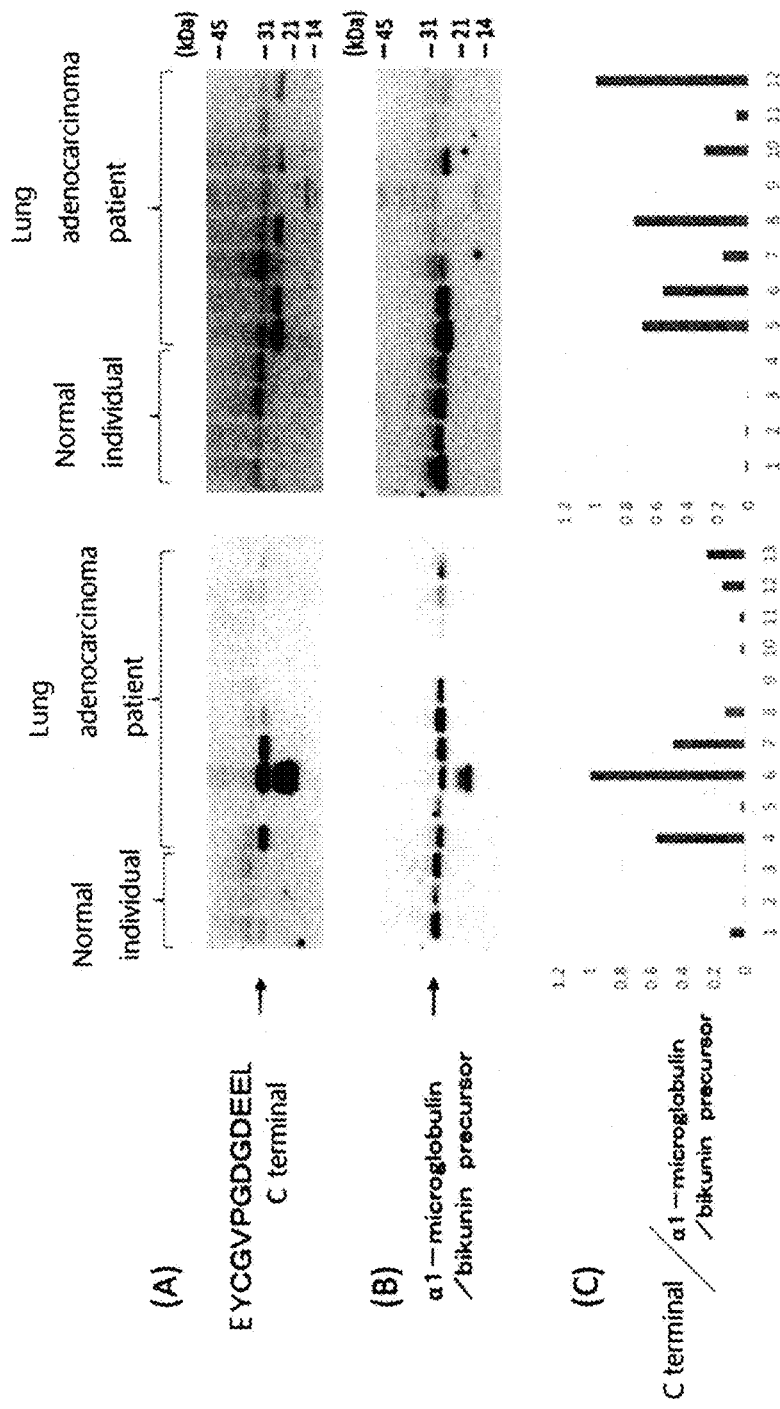
FIG. 1(A) is a view showing the result of western blotting performed on urine samples using a polyclonal antibody against a protein fragment having a C-terminal amino acid sequence of EYCGVPGDGDEEL (SEQ ID NO: 17).
FIG. 1(B) is a view showing the result of western blotting performed on urine samples using a commercially available AMBP antibody.
FIG. 1(C) is a diagram showing the relative amount of (A)/(B).

The adenocarcinoma detection method of the present invention is based on new discovery by the present inventors. That is, the present inventors have found that, in the body of adenocarcinoma patients, one or more of several kinds of specific proteins are cleaved at the site where the proteins are not cleaved in healthy individuals, and various types of defective proteins or proteins having breaks may be increased. Hence, they have found that a phenomenon such as a deletion in the C-terminal part or the N-terminal part, a peptide bond break at an abnormal position or a deletion of amino acids accompanied by the break is observed in the specific proteins.

Such abnormal cleavage is thought to be due to the presence of adenocarcinoma-specific protease. Therefore, in the present invention, healthy individuals and adenocarcinoma patients can be distinguished and evaluated in vitro by using breaks or deletions in the specific proteins due to such abnormal cleavage as indicators. Meanwhile, the increased abnormal cleavage in specific proteins can be evaluated by distinguishing between healthy individuals and adenocarcinoma patients using the decrease in the amount of normal protein (including the relative amount ratio) as an indicator.

The present invention is an adenocarcinoma detection method including a step of detecting in vitro a presence or absence of an abnormal cleavage in one or two or more specific proteins in a test subject-derived sample. Here, the specific protein are derived from any one of the proteins selected from the group consisting of the following (i) to (x):
(i) α-1-antitrypsin
(ii) α-1-microglobulin/bikunin precursor
(iii) CD59
(iv) Fibronectin
(v) Lectin, Mannose-Binding 2
(vi) Vasorin
(vii) WAP four-disulfide core domain protein 2
(viii) Membrane-bound carboxypeptidase M
(ix) Deoxyribonuclease-1; and
(x) WNT1-inducible-signaling pathway protein 2.

In the present specification, the "abnormal cleavage" of the specific protein is not limited, and results in a primary structure, secondary structure, or tertiary structure, different from the normal structure of the specific protein. Examples the abnormal cleavage include a cleavage resulting in one or more breaks in a peptide bond in the specific protein and a cleavage resulting in a deletion of one or two or more amino acid residues at one or more sites of the specific protein.

Although not limited thereto, a protein having a deletion of an amino acid residue on the C-terminal side of the specific protein or a protein having a deletion of an amino acid residue on the N-terminal side of the specific protein can be generated by the "abnormal cleavage". Alternatively, the "abnormal cleavage" results in a break of a peptide bond between amino acid residues in a protein or a deletion of an amino acid at any intermediate position.

In one embodiment of the "abnormal cleavage" of a specific protein, the breaking of a peptide bond exposes an amino acid residue at a new cleavage site. However, the amino acid may not be lost from the original protein due to a disulfide bond or the like. In such a case, in an untreated sample extracted from the living body, the deletion or fragmentation of the specific protein may not occur. The abnormal cleavage of the present invention also includes such cleavage. Alternatively, as described above, the bound state of the original protein is maintained by, for example, a disulfide bond. However, when the peptide bond is broken and is further devoid of one or two or more amino acid residues, this causes a case in which the amino acid residues in the protein are deleted at any intermediate position.

In associated with the specific protein, normal post-translational processing is not the abnormal cleavage herein.

In the present specification, the term "test subject" refers to a mammal as a cancer detection target, and is preferably, but not limited to, a dog, a cat, a mouse or a human.

In the present specification, the term "adenocarcinoma" refers to cancer that occurs in the secretory gland tissue of each organ in the body. "Adenocarcinoma" includes, but not limited to, lung adenocarcinoma, liver adenocarcinoma, pancreatic adenocarcinoma, lymphatic adenocarcinoma, uterine adenocarcinoma, seminal adenocarcinoma, and gastric adenocarcinoma. The detection method of the present invention is particularly preferably used for the detection of lung adenocarcinoma. In the present invention, adenocarcinoma may be in any of the clinical stages IA, IB, IIA, IIB, IIIA, IIIB, and IV. Early-stage adenocarcinoma or early-stage lung adenocarcinoma refers to any of the clinical stages IA, IB, IIA, and IIB.

In the present specification, the term "test subject-derived sample" refers to a body fluid derived from a test subject, and refers to a body fluid concentrate, a body fluid diluent, or another appropriately treated liquid, in addition to the body fluid itself. Here, the body fluid refers to urine, blood (whole blood, plasma or serum), sputum, sweat, spinal fluid, digestive juice or ascitic fluid, but the fluid is not limited thereto. The body fluid is preferably urine or blood, and particularly preferably urine. Here, the urine can be any of early morning midstream urine, pooled urine, and occasional urine. The collection amount of body fluid such as urine or blood is 10 µl to 200 ml, preferably 100 µl to 100 ml, and more preferably 1 ml to 100 ml.

Here, treatment of body fluid more specifically refers to pretreatment such as concentration, dilution, fractionation, and desalination, and addition of preservatives (e.g., glycerin), stabilizers (e.g., protease inhibitors), and antiseptics. The treatment also includes a process of returning the temperature to normal temperature after a refrigerating or freezing treatment, a process of performing an appropriate treatment either before or after the refrigerating or freezing treatment, and the like. Further, for example, when the body fluid is blood, an anticoagulant treatment can be performed as an appropriate treatment. It is also possible to combine these treatments.

When the body fluid is urine, it is preferable to perform the operation including concentration as the pretreatment before the measurement. This concentration method is not particularly limited, and examples thereof include a method using an ultrafiltration membrane with a fraction molecular weight, a freeze concentration method, a decompression or vacuum concentration method, and a heating method. The fraction molecular weight is not limited and, for example, any value such as 3 kD, 10 kD, 30 kD or 50 kD can be used.

For example, when the body fluid is urine, concentration is a useful pretreatment since the concentration of total protein in primitive urine is about 0.001 g/dL to 0.6 g/dL. The primitive urine can be concentrated to 200 to 250-folds and used for analysis. Although this concentrated solution can be directly used for measurement, the solution can also be used for measurement by further diluting the total protein. For example, depending on the measurement method such as western blotting, the solution can be adjusted to about 0.1 µg to 10 µg/µl for measurement.

In the concentration, Vivaspin (registered trademark, manufactured by Sartorius Japan K.K.), Amicon Ultra (manufactured by Merck KGaA), and the like can be used according to the manufacturer's instructions.

Distilled water and a buffer solution can be used for dilution and can also be used for adjustment of the concentrated urine.

The size and length of a deletion of a specific protein is not particularly limited as long as, when compared in the primary structure, there is a deletion in the C-terminal and N-terminal parts of the full-length protein derived from the specific protein or a deletion of amino acid residues at the intermediate position. Here, the term "there is a deletion in the C-terminal and N-terminal parts or at the intermediate position" means that the C-terminal and N-terminal sides of the protein are usually short and the amino acid residues to be present at the intermediate position are deleted, compared with a protein of a normally functioning unit.

In the present specification, when the sequence of a protein fragment is specified, each written symbol means an ordinary character used as a one-letter expression of amino acid residue.

Specific examples are as follows.

| A | Ala | Alanine |
|---|-----|---------|
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

In the present invention, a step of detecting in vitro a presence or absence of an abnormal cleavage in one or two or more specific proteins in a test subject-derived sample is not limited, and the step can be preferably a step including at least one selected from the group consisting of the following (1) to (4):

(1) detecting a decrease in an amount of a protein having a normal structure of the specific protein in the test subject-derived sample;

(2) detecting an amount or presence of a protein fragment having a deletion of an amino acid residue on a C-terminal side of the specific protein in the test subject-derived sample;

(3) detecting an amount or presence of a protein fragment having a deletion of an amino acid residue on an N-terminal side of the specific protein in the test subject-derived sample; and (4) detecting an amount or presence of a protein having a break or deletion in any intermediate site of an amino acid sequence of the specific protein in the test subject-derived sample.

Although not limited thereto, one embodiment of the adenocarcinoma detection method of the present invention includes detecting a decrease in an amount of a protein having a normal structure of one or two or more of specific protein in a test subject-derived sample. Specifically, for example, the amount of the specific protein having a normal structure is measured by the presence or absence of the amino acid sequence at the C-terminal part and/or the N-terminal part of the specific protein so that it is possible to detect whether or not the amount of the protein having a normal structure is relatively reduced as compared with healthy individuals.

Although not limited thereto, another embodiment of the adenocarcinoma detection method of the present invention includes detecting in vitro a specific protein fragment using a test subject-derived sample. In such a case, detection of the specific protein fragment can be a detection of a protein fragment present in a fragmented state in the test subject-derived sample and/or, for example, a protein fragment generated after subjecting the test subject-derived sample to a reduction treatment or the like.

Specifically, in a step of measuring in vitro the amount of one or two or more specific proteins, it is preferable that the specific protein fragments are fragments which are derived from any one of the proteins selected from the group consisting of the following (i) to (x) and which are derived from a protein having a deletion in the C-terminal side compared with the full length of the protein, or fragments derived from a protein with a break and/or an amino acid deletion at the intermediate site.

In the present specification, the C-terminal sequence of the specific protein fragment is expressed as, for example, "a protein fragment having a C-terminal amino acid sequence of GTEAAGAMF", SEQ ID NO: 11. In the full-length protein, this case indicates that an amino acid residue originally present on the side closer to the C-terminus than F at the right end is deleted (defective), and the amino acid residue may be present or absent on the side closer to the N-terminus than G.

It is preferable that the specific protein fragment is at least one selected from the group consisting of the followings:
(a) a protein fragment having a C-terminal amino acid sequence of GTEAAGAMF, SEQ ID NO: 11;
(b) a protein fragment having a C-terminal amino acid sequence of CVLFPYGG, SEQ ID NO: 12;
(c) a protein fragment having a C-terminal amino acid sequence of EYCGVPG, SEQ ID NO: 13;
(d) a protein fragment having a C-terminal amino acid sequence of EYCGVPGDG, SEQ ID NO: 14;
(e) a protein fragment having a C-terminal amino acid sequence of EYCGVPGDGE, SEQ ID NO: 15;
(f) a protein fragment having a C-terminal amino acid sequence of EYCGVPGDGEE, SEQ ID NO: 16;
(g) a protein fragment having a C-terminal amino acid sequence of EYCGVPGDGEEL, SEQ ID NO: 17;
(h) a protein fragment having a C-terminal amino acid sequence of EYCGVPGDGEELL, SEQ ID NO: 18;
(i) a protein fragment having a C-terminal amino acid sequence of GECVPGEQEPEP, SEQ ID NO: 19;
(j) a protein fragment having a C-terminal amino acid sequence of GECVPGEQEPEPILIP, SEQ ID NO: 20;
(k) a protein fragment having a C-terminal amino acid sequence of DLCNFNEQL, SEQ ID NO: 21;
(n) a protein fragment having a C-terminal amino acid sequence of FGFCPMA, SEQ ID NO: 22;
(p) a protein fragment having a C-terminal amino acid sequence of EGSCPQVNINFPQLG, SEQ ID NO: 23;
(q) a protein fragment having a C-terminal amino acid sequence of LPTGYY, SEQ ID NO: 24;
(r) a protein fragment having a C-terminal amino acid sequence of YLQGSSVQL, SEQ ID NO: 25;
(s) a protein fragment having a C-terminal amino acid sequence of EGSCPQVNIN, SEQ ID NO: 26;
(t) a protein fragment having a C-terminal amino acid sequence of ENYNQYDLN, SEQ ID NO: 27;
(u) a protein fragment having a C-terminal amino acid sequence of GAVVPDSALPFNFQAAY, SEQ ID NO: 28;
(v) a protein fragment having a C-terminal amino acid sequence of EGSCPQVNINFPQLGL, SEQ ID NO: 29;
(w) a protein fragment having a C-terminal amino acid sequence of GALCLLAEDDS, SEQ ID NO: 30;
(x) a protein fragment having a C-terminal amino acid sequence of EYCGVPGD, SEQ ID NO: 31; and
(y) a protein fragment having a C-terminal amino acid sequence of GECVPGEQEPE, SEQ ID NO: 32.

Further, it is possible to detect early-stage lung adenocarcinoma by measuring in vitro at least one selected from the group consisting of the following specific protein fragments:
(b) a protein fragment having a C-terminal amino acid sequence of CVLFPYGG, SEQ ID NO: 12;
(c) a protein fragment having a C-terminal amino acid sequence of EYCGVPG, SEQ ID NO: 13;
(d) a protein fragment having a C-terminal amino acid sequence of EYCGVPGDG, SEQ ID NO: 14;
(e) a protein fragment having a C-terminal amino acid sequence of EYCGVPGDGE, SEQ ID NO: 15;
(f) a protein fragment having a C-terminal amino acid sequence of EYCGVPGDGEE, SEQ ID NO: 16;
(g) a protein fragment having a C-terminal amino acid sequence of EYCGVPGDGEEL, SEQ ID NO: 17;
(h) a protein fragment having a C-terminal amino acid sequence of EYCGVPGDGEELL, SEQ ID NO: 18;
(i) a protein fragment having a C-terminal amino acid sequence of GECVPGEQEPEP, SEQ ID NO: 19;
(j) a protein fragment having a C-terminal amino acid sequence of GECVPGEQEPEPILIP, SEQ ID NO: 20;
(k) a protein fragment having a C-terminal amino acid sequence of DLCNFNEQL, SEQ ID NO: 21;
(p) a protein fragment having a C-terminal amino acid sequence of EGSCPQVNINFPQLG, SEQ ID NO: 23;
(s) a protein fragment having a C-terminal amino acid sequence of EGSCPQVNIN, SEQ ID NO: 26;
(t) a protein fragment having a C-terminal amino acid sequence of ENYNQYDLN, SEQ ID NO: 27;
(u) a protein fragment having a C-terminal amino acid sequence of GAVVPDSALPFNFQAAY, SEQ ID NO: 28;
(v) a protein fragment having a C-terminal amino acid sequence of EGSCPQVNINFPQLGL, SEQ ID NO: 29;
(w) a protein fragment having a C-terminal amino acid sequence of GALCLLAEDDS, SEQ ID NO: 30;
(x) a protein fragment having a C-terminal amino acid sequence of EYCGVPGD, SEQ ID NO: 31; and
(y) a protein fragment having a C-terminal amino acid sequence of GECVPGEQEPE, SEQ ID NO: 32.

Here, the number of amino acid residues in the specific protein fragment is not particularly limited, and is at least 6, may be at least 7, preferably at least 10 or more, and more preferably at least 50 or more. The upper limit of the size of a protein fragment is not particularly limited, and is less than the size of the full-length protein from which each protein fragment is derived. For example, although not limited thereto, the protein fragment has a structure which is lacking in the C-terminal side, compared with the full-length protein from which each protein fragment is derived. The protein fragment is not particularly limited as long as the size is less than the full length, and in some cases, the protein fragment may be present as a short fragment such as 200 residues or less, preferably 100 residues or less.

Further, it is possible to detect a presence or an increase in relative amount of a protein having a deletion of an amino acid residue on an N-terminal side of the specific protein in the test subject-derived sample; and detect a liberated protein fragment on a C-terminal side lacking in an N-terminal side in order to detect the presence or the increase in the relative amount of a protein having a break or deletion in any intermediate site of an amino acid sequence of the specific protein in the test subject-derived sample. The fragment is detected so that it is also possible to indirectly detect the protein fragments (a) to (y) or to detect the presence of a protein fragment in which the N terminus is defective in vivo.

The molecular weight of the specific protein fragment of the present invention is not limited as long as the molecular weight is less than that of the full-length protein. However, depending on the method of detecting adenocarcinoma using a specimen such as urine, the molecular weight is, for example, 3 kDa or more and less than the full length, preferably 10 kDa or more and less than the full length.

Further, these specific protein fragments include protein fragments subjected to post-translational modification such as glycosylation or phosphorylation as long as the specific protein fragments respectively have the sequences described above.

Specifically, the specific protein fragments may be fragments derived from the full-length proteins shown below.
(i) α-1-antitrypsin
(ii) α-1-microglobulin/bikunin precursor
(iii) CD59
(iv) Fibronectin
(v) Lectin, Mannose-Binding 2
(vi) Vasorin
(vii) WAP four-disulfide core domain protein 2
(viii) Membrane-bound carboxypeptidase M
(ix) Deoxyribonuclease-1; or
(x) WNT1-inducible-signaling pathway protein 2

These proteins normally function in their original length in vivo. It is considered that, the proteins are cleaved by an enzyme whose activity is enhanced, particularly in adenocarcinoma (e.g., a matrix metalloprotease group), whereby secondary fragmentation and amino acid deletion can be increased.

For example, (ii) α-1-microglobulin/bikunin precursor includes α-1-microglobulin, inter-α-trypsin inhibitor light chain, and trypstatin. The three mature proteins normally function in their original length in vivo. The mature proteins are specifically expressed, particularly in adenocarcinoma, or are cleaved by an enzyme whose activity is enhanced (e.g., the matrix metalloprotease group), whereby secondary fragmentation and amino acid deletion can be increased.

Hereinafter, the proteins described in (i) to (x) and sequences of specific protein fragments derived from these proteins will be described by exemplifying them with reference to specific sequences (SEQ ID NOs: 1 to 10 in the sequence listing) contained in a specific database. As will be appreciated by those skilled in the art, these sequences as well as the position and number of amino acid residues in these sequences may vary from individual to individual, and the published sequences may also differ depending on the database. Each of the sequences is to explain the present invention and does not limit the present invention.

(aa) A protein fragment whose C-terminal sequence is GTEAAGAMF (SEQ ID NO: 11) can be derived from α-1-antitrypsin. α-1-antitrypsin is a neutrophil elastase inhibitor, and the main function is to protect the lung from protease-mediated tissue destruction. The sequence of α-1-antitrypsin precursor is, for example, a sequence of UniProtKB P01009(A1AT_HUMAN) (SEQ ID NO: 1 in the sequence listing). The specific protein fragment may be, when described with this sequence, a protein fragment having a C-terminal part which coincides with amino acid residues at positions 368 to 376 and a C-terminal side deleted from position 377.

(bb) A protein fragment whose C-terminal sequence is CVLFPYGG (SEQ ID NO: 12) can be derived from α-1-microglobulin/bikunin precursor.

(cc) A protein fragment whose C-terminal sequence is EYCGVPG (SEQ ID NO: 13) can be derived from α-1-microglobulin/bikunin precursor.

(dd) A protein fragment whose C-terminal sequence is EYCGVPGDG (SEQ ID NO: 14) can be derived from α-1-microglobulin/bikunin precursor.

(ee) A protein fragment whose C-terminal sequence is EYCGVPGDGDE (SEQ ID NO: 15) can be derived from α-1-microglobulin/bikunin precursor.

(ff) A protein fragment whose C-terminal sequence is EYCGVPGDGDEE (SEQ ID NO: 16) can be derived from α-1-microglobulin/bikunin precursor.

(gg) A protein fragment whose C-terminal sequence is EYCGVPGDGDEEL (SEQ ID NO: 17) can be derived from α-1-microglobulin/bikunin precursor.

(hh) A protein fragment whose C-terminal sequence is EYCGVPGDGDEELL (SEQ ID NO: 18) can be derived from α-1-microglobulin/bikunin precursor.

(ii) A protein fragment whose C-terminal sequence is GECVPGEQEPEP (SEQ ID NO: 19) can be derived from α-1-microglobulin/bikunin precursor.

(jj) A protein fragment whose C-terminal sequence is GECVPGEQEPEPILIP (SEQ ID NO: 20) can be derived from α-1-microglobulin/bikunin precursor.

(xx) A protein fragment whose C-terminal sequence is EYCGVPGD (SEQ ID NO: 31) can be derived from α-1-microglobulin/bikunin precursor.

(yy) A protein fragment whose C-terminal sequence is GECVPGEQEPE (SEQ ID NO: 32) can be derived from α-1-microglobulin/bikunin precursor.

Here, α-1-microglobulin (α1-m) is a glycoprotein having a molecular weight of about 30,000. The sequence of the protein can be, for example, a sequence represented by UniProtKB P02760 (SEQ ID NO: 2 in the sequence listing). The protein having a normal structure is a protein having at least Asn at position 352 of SEQ ID NO: 2 in the sequence listing as the C-terminal. When described with, for example, the sequence of UniProtKB P02760, the specific protein fragment (bb) can be a protein fragment having inter-α-trypsin inhibitor light chain or amino acid residues at positions 312 to 319 contained in trypstatin and a defective C-terminal side, or a protein fragment containing only inter-α-trypsin inhibitor light chain part or containing only trypstatin. When described with the sequence of UniProtKB P02760, the specific protein fragments (cc) to (hh) and (xx), although not limited thereto, are protein fragments which have any of the following amino acid sequences: an amino acid sequence of amino acid residues at positions 335 to 341 or positions 335 to 342; an amino acid sequence of amino acid residues at positions 335 to 343 in this sequence; an amino acid sequence of amino acid residues at positions 335 to 345 in this sequence; an amino acid sequence of amino acid residues at positions 335 to 346 in this sequence; an amino acid sequence of amino acid residues at positions 335 to 347 in this sequence; and an amino acid sequence of amino acid residues at positions 335 to 348 in this sequence; and in which the amino acid sequence has a defective C-terminal side and contains only inter-α-trypsin inhibitor light chain part, or has a deletion in the C-terminus and contains only trypstatin. In the specific protein fragments (yy), (ii) or (jj), when described with the sequence of UniProtKB P02760, each of the fragments can be a protein fragment having a sequence of amino acid residues at positions 186 to 196 or positions 186 to 197 or a sequence of amino acid residues at positions 186 to 201, and having a defective C-terminal side.

(kk) A protein fragment whose C-terminal sequence is DLCNFNEQL (SEQ ID NO: 21) can be derived from CD59. Here, the CD59 molecule is known as a complement regulatory factor and is a molecule that inhibits the formation of a membrane damage complex by acting on C9. The sequence of the protein can be, for example, a sequence represented by UniProtKB P13987(CD59_HUMAN) (SEQ ID NO: 3 in the sequence listing). The specific protein fragment (kk) can be, when described with the sequence represented by UniProtKB P13987, a protein fragment having amino acid residues at positions 92 to 100 and a C-terminal side deleted from position 101.

(nn) A protein fragment whose C-terminal sequence is FGFCPMA (SEQ ID NO: 22) can be derived from fibronectin. Fibronectin is a glycoprotein with a relatively large molecular weight, i.e., a cell adhesion molecule. It is thought that the cell adhesion molecule has functions such as the adhesion of cells to the extracellular matrix, the formation and retention of connective tissue, wound healing, and the formation and maintenance of the form and division of tissues and organs during embryogenesis. The sequence of fibronectin is, for example, a sequence of UniProtKB P02751 (FINC_HUMAN) (SEQ ID NO: 4 in the sequence listing). Although not limited thereto, the specific protein fragment can be, for example, when described with the sequence of UniProtKB P02751, a protein fragment having amino acid residues at positions 458 to 464 and a C-terminal side deleted from position 465.

(qq) A protein fragment whose C-terminal sequence is LPTGYY (SEQ ID NO: 24) can be derived from Lectin, Mannose-Binding 2. Lectin, Mannose-Binding 2 has a sequence of UniProtKB-Q12907 (LMAN2_HUMAN) (SEQ ID NO: 5 in the sequence listing). Although not limited thereto, the specific protein fragment can be, for example, when described with this sequence, a protein fragment having amino acid residues at positions 247 to 252 and a defective C-terminal side.

(rr) A protein fragment whose C-terminal sequence is YLQGSSVQL (SEQ ID NO: 25) can be derived from vasorin. Vasorin is a type 1 membrane protein expressed specifically in vascular smooth muscle cells. The sequence of vasorin is, for example, a sequence of UniProtKB Q6EMK4 (VASN_HUMAN) (SEQ ID NO: 6 in the sequence listing). Although not limited thereto, the specific protein fragment can be, for example, when described with this sequence, a protein fragment having amino acid residues at positions 483 to 491 and a defective C-terminal side.

(ss) A protein fragment whose C-terminal sequence is EGSCPQVNIN (SEQ ID NO: 26) can be derived from WAP four-disulfide core domain protein 2.

(pp) A protein fragment whose C-terminal sequence is EGSCPQVNINFPQLG (SEQ ID NO: 23) can be derived from WAP four-disulfide core domain protein 2.

(vv) A protein fragment whose C-terminal sequence is EGSCPQVNINFPQLGL (SEQ ID NO: 29) can similarly be derived from WAP four-disulfide core domain protein 2. For example, the sequence of WAP four-disulfide core domain protein 2 is a sequence of UniProtKB Q14508 (WFDC2_HUMAN) (SEQ ID NO: 7 in the sequence listing). The protein having a normal structure is a protein having at least Phe at position 124 of SEQ ID NO: 7 in the sequence listing as the C-terminus. Although not limited thereto, the specific protein fragment can be, for example, when described with this sequence, a protein fragment having amino acid residues at positions 77 to 86, amino acid residues at positions 77 to 91 or positions 77 to 92, and a defective C-terminal side.

(tt) A protein fragment whose C-terminal sequence is ENYNQYDLN (SEQ ID NO: 27) can be derived from Membrane-bound carboxypeptidase M. Membrane-bound carboxypeptidase M is an exopeptidase that cleaves one residue from a C-terminal side of a substrate. This sequence can be, for example, a sequence of UniProtKB P14384 (CBPM_HUMAN) (SEQ ID NO: 8 in the sequence listing). Although not limited thereto, the specific protein fragment can be, for example, when described with this sequence, a protein fragment having amino acid residues at positions 145 to 153 and a defective C-terminal side.

(uu) A protein fragment whose C-terminal sequence is GAVVPDSALPFNFQAAY (SEQ ID NO: 28) can be derived from deoxyribonuclease-1. This sequence can be, for example, a sequence of UniProtKB P24855 (DNAS1_HUMAN) (SEQ ID NO: 9 in the sequence listing). Although not limited thereto, the specific protein fragment can be, for example, when described with this sequence, a protein fragment having amino acid residues at positions 245 to 261 and a defective C-terminal side.

(ww) A protein fragment whose C-terminal sequence is GALCLLAEDDS (SEQ ID NO: 30) can be derived from WNT1-inducible-signaling pathway protein 2. This sequence can be, for example, a sequence of UniProtKB-O76076 (WISP2_HUMAN) (SEQ ID NO: 10 in the sequence listing). Although not limited thereto, the specific protein fragment can be, for example, when described with this sequence, a protein fragment having amino acid residues at positions 88 to 98 and a defective C-terminal side.

In the method for detecting abnormal cleavage of the present invention, the mass of the specific protein having a normal structure or its presence and the amount of the specific protein fragment or its presence can be determined by measuring the mass, volume, and concentration of the specific protein and the specific protein fragment contained in a body fluid, i.e., a test subject-derived sample. Further, these amounts can be expressed by fluorescence intensity, absorbance, MS/MS spectrum intensity, and the like.

Further, the detection method of the present invention is not particularly limited as long as the detection method is a method for detecting abnormal cleavage in a test subject-derived sample or a method for detecting a protein having a normal structure. For example, in addition to a method for detecting by mass spectrometry, there is a method for detecting by an immunochemical measurement method using an antibody (radioimmunoassay, enzyme immunoassay, Western blotting, etc.).

The method by mass spectrometry is not particularly limited as long as the method is a method for detecting a specific protein having a normal structure in a test subject-derived sample or a specific protein fragment derived from abnormal cleavage. Specifically, for example, there is a method for collecting a sample, digesting the sample with an enzyme after pretreatment and/or reduction treatment, labeling the sample with an isotope or the like, and then measuring the amount of only the peptide derived from the C-terminus by MS/MS. More specifically, although not limited thereto, when the test subject-derived sample is urine, urine is collected, the urine specimen is subjected to concentration as a pretreatment to obtain a specimen, this concentrated specimen is subjected to reductive alkylation, and then the resulting specimen is digested with trypsin in the presence of $H_2^{18}O$, so that peptides derived from trypsin-digested fragments can be labeled with a stable isotope. Then, after purification by desalting and ion exchange chromatography, only trypsin-digested peptides derived from the C-terminus are measured by Nano-LC-MALDI-MS/MS. This peptide information is analyzed so that it is possible to distinguish and detect the protein having a normal structure or the specific protein fragment derived from abnormal cleavage. In addition to this, for example, a method for measuring a specific protein fragment can be employed in which a protein in a concentrated sample with Lys-C is subjected to enzymatic digestion, the N-terminus of all the digested peptides is blocked by phenyl isocyanate or the TMPP reagent (N-Succinimidyloxycarbonyl-methyl)tris (2,4,6-trimethoxyphenyl) phosphonium bromide) to obtain a peptide having a C-terminus other than lysine, and an MS/MS analysis is preformed using amass spectrometer.

When the amount of the specific protein fragment is measured by multiple reaction monitoring (MRM), it is also possible to use, for example, a high performance liquid chromatography/triple quadrupole mass spectrometer (QTRAP® 5500 System (AB Sciex.)) or LCMS-8030 (manufactured by Shimadzu Corporation).

In the method by radioimmunoassay and enzyme immunoassay, it is desirable to use an antibody that specifically recognizes an exposed part of an amino acid derived from abnormal cleavage, a C-terminal part of a specific protein fragment or a deletion part of a specific amino acid and can distinguish each of the parts from the corresponding protein having a normal structure. An antibody that specifically recognizes a specific protein or antigen derived from the specific protein can be produced in such a manner that, although not limited thereto, peptides corresponding to the corresponding C-terminal part, the N-terminal part, another part, and a deletion part are administered to chickens, rats, mice, rabbits or the like, followed by immunization. In order to suppress the cross-linking reactivity with the corresponding full-length type protein, an antigen may be immobilized on a column and an antibody may be produced by purifying a polyclonal antibody obtained from the immunized animals. A monoclonal antibody that specifically recognizes a site containing a C-terminal amino acid or a deletion part of each fragment may be produced. The method for producing a monoclonal antibody is known to those skilled in the art. For example, hybridomas having a proliferative capacity are produced by cell fusion of antibody-producing cells obtained from the above immunized animals with myeloma cells. In particular, only the clone is selected in which an antibody having specificity to the C-terminal amino acid is produced. The cells are cultured, secreting antibodies are purified, and the purified antibodies are used as the antibodies of the present invention.

In Western blotting, although not limited thereto, specifically, a test subject-derived sample is subjected to SDS-PAGE and transferred to a nitrocellulose membrane or a PVDF membrane. The transferred membrane is blocked with skim milk or the like, and then treated with a primary antibody specifically recognizing the C-terminal amino acid of each protein or protein fragment or a site containing a deletion part. Subsequently, the membrane is treated with a horseradish peroxidase (HRP)-labeled secondary antibody recognizing the primary antibody, and an electrophoretic band of a target protein fragment is detected by color development or chemiluminescence derived from the enzymatic activity of HRP. In the enzyme immunoassay, for example, a specimen is treated with the primary antibody and the HRP-labeled secondary antibody in a 96-well plate, and a target protein fragment is detected by color development or chemiluminescence derived from the enzymatic activity of HRP. It is also possible to use a sandwich method or the like.

In order to correct variations in results due to changes in the metabolic state of a test subject, the abundance of an abnormal cleavage-derived deletion and a protein fragment in a test subject-derived sample is detected by mass spectrometry, radioimmunoassay, enzyme immunoassay or Western blotting, and then the detected abundance can be compared with the abundance of total protein present in the test subject-derived sample. The amount of total protein in the test subject-derived sample may be quantified using a commercially available protein assay kit such as the BCA method or the Bradford method, and a liquid chromatography method or the like may be used. In addition, the amount of total protein may be compared with the amount of creatinine in urine which is used for correcting the changes in the water content of the urine specimen.

The amount of a specific protein having a normal structure or the amount of a specific protein fragment in a test subject-derived sample can be compared with the abundance of all proteins derived from a specific protein coexisting in a sample and represented by a relative ratio. Alternatively, the abundance of a protein fragment in a test subject-derived sample can be compared with the amount of total protein in the test subject-derived sample and expressed by a relative ratio of the amount of the fragment to the amount of total protein.

In the case of using any of the measurement methods, the presence or absence of an abnormal cleavage in a specific protein can be determined by calculating the fragmentation rate of the specific protein in a test subject sample and judging whether or not the value is greater than a threshold value. Hence, when the fragmentation rate of the specific protein is greater than the threshold value, it can be grasped that the derived test subject has adenocarcinoma.

More specifically, although not limited thereto, for example, the fragmentation rate ($F_n$) of each specific protein is determined by the following calculation formula. When the fragmentation rate of the specific protein in the patient sample is greater than 1, as expressed by the relative ratio ($R_n$), with respect to the average value of the healthy individual group, the specific protein can be determined to be positive.

$$\text{Protein fragmentation rate } (F_n) = C_n/I_n \qquad \text{[Equation 1]}$$

$C_n$: amount of each specific protein fragment
$I_n$: amount of original protein derived from each specific protein fragment $$\text{Relative ratio } (R_n) \text{ of protein fragmentation rates between patient and healthy individual} = F_p/F_h \qquad \text{[Equation 2]}$$

$F_p$: protein fragmentation rate of patient sample
$F_h$: average value of protein fragmentation rates of healthy individual group Here, the amount of each specific protein fragment in $C_n$ refers to an amount of one specific protein fragment (e.g., an amount corresponding to one of the protein fragments having an abnormal C-terminus as shown in Table 3).

The amount of original protein in $I_n$ refers to, for example, an amount of trypsin-digested peptide commonly included in a protein fragment or full-length protein. Here, the measurement method is in accordance with the conditions described in Example 7.

Here, the sequences commonly included are not limited, and the following sequences can be used.

AMBP: TVAACNLPIVR (at positions 283 to 293 of SEQ ID NO: 2 in the sequence listing)

WFDC2: CCSAGCATFCSLPNDK (at positions 61 to 76 of SEQ ID NO: 7 in the sequence listing)

WISP2: CPLGVPLVLDGCGCCR (at positions 39 to 54 of SEQ ID NO: 10 in the sequence listing)

DNAS1: DSHLTAVGK (at positions 64 to 72 of SEQ ID NO: 9 in the sequence listing)

CBPM: DPEITNLINSTR (at positions 107 to 118 of SEQ ID NO: 8 in the sequence listing)

VASN: ESHVTLASPEETR (at positions 315 to 327 of SEQ ID NO: 6 in the sequence listing)

FINC: YSFCTDHTVLVQTR (at positions 398 to 411 of SEQ ID NO: 4 in the sequence listing)

LMAN2: DHDTFLAVR (at positions 210 to 218 of SEQ ID NO: 5 in the sequence listing)

CD59: FEHCNFNDVTTR (at positions 67 to 78 of SEQ ID NO: 3 in the sequence listing)

When the amount of a protein having a normal structure in a test subject-derived sample is significantly decreased as compared with a specimen sample (healthy sample) of a healthy individual, the target person is judged as an adenocarcinoma patient. Here, the term "significantly decreased" means that the relative ratio of the protein having the normal structure is decreased to, for example, 0.9 times or less, preferably 0.8 times or less, more preferably 0.6 times or less, as compared with a healthy individual specimen. Alternatively, in the case of using an antibody, the term means that a decrease in the amount which is recognizable from the intensity of label or the like is 0.8 times or less, preferably 0.6 times or less, as compared with a healthy individual specimen.

When the amount of a specific protein fragment in a test subject-derived sample is significantly increased as compared with a specimen sample (healthy sample) of a healthy individual, the target person is judged as an adenocarcinoma patient. Here, the term "significantly increased" means that the relative ratio of the fragmentation rate is increased to a value greater than 1, 1.25 times or more, preferably 1.5 times or more, more preferably 2.0 times or more, as compared with a healthy individual specimen.

In the case of using an antibody, the term means that the increase in the amount of a specific protein fragment that can be recognized from the intensity of a label or the like is greater than 1, preferably 1.2 times or more, more preferably about 1.5 times or more, as compared with a healthy individual specimen. Note that the numerical value of the comparison here refers to a value after correction using an internal standard or the like.

The amount of a specific protein having a normal structure or the amount of a specific protein fragment in a test subject-derived sample from a healthy individual can be determined in accordance with the preparation and measurement method of the test subject-derived sample.

In a particularly preferred embodiment of the present invention, one or two or more specific proteins contains at least (ii) α-1-microglobulin/bikunin precursor, and a step of detecting in vitro a presence or absence of an abnormal cleavage includes detecting a decrease in an amount of a protein having a normal structure which is derived from α-1-microglobulin/bikunin precursor present in a test subject sample, and/or an amount or presence of a protein fragment derived from α-1-microglobulin/bikunin precursor. Here, for example, an antibody recognizing the C-terminal part of (g) EYCGVPGDGDEEL (SEQ ID NO: 17) can be suitably used.

In a particularly preferred embodiment of the present invention, one or two or more specific proteins include at least (vii) WAP four-disulfide core domain protein 2, and the step of detecting in vitro the presence or absence of the abnormal cleavage includes detecting a cleavage of a peptide bond in any of the amino acid sequences at positions 80 to 93 of SEQ ID NO: 7 in the sequence listing, or a deletion of an amino acid residue around the cleavage site.

EXAMPLES

Subsequently, the present invention will be specifically described with reference to examples, however the present invention is not limited to the following examples.

[Example 1] Collection of Body Fluids

Among patients with pulmonary nodule shadows or tumor shadows, suspected of primary lung cancer by chest image examination, patients diagnosed with lung adenocarcinoma were selected by surgery, transbronchial biopsy, lymph node biopsy or cytology. Early morning midstream urine was collected from selected lung adenocarcinoma patients and healthy individuals using sterile cups. The collected urine samples were stored at −80° C. until analysis.

C-terminal protein fragments in urine from 85 cases with lung adenocarcinoma and 25 healthy individuals were comprehensively analyzed. A breakdown of clinical stages of the cases with lung adenocarcinoma showed that 18 cases were in clinical stage IA, 5 cases were in clinical stage IB, 1 case was in clinical stage IIA, 0 case was in clinical stage IIB, 6 cases were in clinical stage IIIA, 5 cases were in clinical stage IIIb, and 50 cases were in clinical stage IV. The clinical stage was judged according to the criteria described in "General Rule for Clinical and Pathological Record of Lung Cancer, The 7th Edition" edited by The Japan Lung Cancer Society (KANEHARA & Co., LTD.). The cases with lung adenocarcinoma (18 cases in stage IA, 5 cases in stage IB, and 1 case in stage IIA) were defined as cases with early-stage lung adenocarcinoma.

[Example 2] Detection by Mass Spectrometry

Urine samples (~50 mL) were collected and markers were searched by the procedures of pretreatment, acquisition of analytical data, and statistical analysis. In the pretreatment, urine samples were concentrated to 200 to 250-folds using Amicon Ultra-15 (10 kDa molecular weight cut-off) and Amicon Ultra-4 (10 kDa molecular weight cut-off) (Merck KGaA) and washed 3 times with 3 mL of triethylammonium hydrogencarbonate solution containing 100 mM NaCl, thereby removing low molecular weight molecules. Thereafter, concentrated specimens were obtained. The proteins in the concentrated specimens were quantified. The concentrations of all the specimens were adjusted to 10 mg/mL of total protein using a buffer solution and the resulting specimens were used in the subsequent analysis process. Subsequently, the samples were subjected to reductive alkylation and then digested with trypsin in a buffer prepared with a constant concentration of $H_2^{18}O$ (method for labeling the C-terminus of a peptide with a stable isotope). After desalting and purification, the samples were labeled with iTRAQ (8-plex, AB Sciex.), eight specimens were mixed, desalted, and purified. Thereafter, only C-terminal trypsin-digested peptides derived from protein fragments were fractionated by ion exchange chromatography (LC column: PolySULFO-ETHYL A™ (PolyLC Inc. USA), with an inner diameter of 4.6 mm and a length of 50 mm; flow rate: 0.4 mL/min; solvent: a solution of 20% acetonitrile/phosphoric acid (pH 2.55), with respect to the solvent, the concentration of a solution of 20% acetonitrile/5 mM monopotassium phosphate and 0.5 M NaCl (pH 2.55) was stepwise increased (0 to 100%) for separation). After desalting and purification of the fractions, Nano-LC (LC column with an inner diameter of 75 μm and a length of 100 mm, filler: Inertsil C18 (particle diameter of 3 μm); flow rate: 250 nL/min; solvent: a 0.1% trifluoroacetic acid solution)/MALDI-MS/MS (AB Sciex.) was used to elute the fractions by acetonitrile concentration gradient (3-80%), the fractions were measured, and then only C-terminal trypsin-digested peptides were selected and extracted (independent development program "iSpec"; Reference: Fernandez-de-Cossio J., Takao T. et al. Rapid Commun. Mass Spectrom. 18, 2465-2472 (2004)). Based on the intensity of the control peak (m/z 113, equally spiked for each assay) in reporter peaks related to comparative determination included in MS/MS spectra (m/z 113 to 119, and 121), other reporter peaks were standardized, and then the comparison between the assays was performed. As a specific evaluation criterion, for the qualification, an assay was adopted in which MS/MS spectra with five or more peaks with a certain intensity or more were selected and the number of proteins identified based on those MS/MS spectra was 50 more. Quantitative values of only the assay in which the peak intensity of the reference reporter peak (m/z 113) was greater than 10 and the number of MS/MS spectra was 300 or more were used for quantification. Only data satisfying these qualification and quantification criteria is used for statistical analysis so that comparison accuracy between assays can be improved, and as a result, the accuracy of statistical analysis can be improved.

[Example 3] Selection of Markers

Regarding the peak intensity (Example 2) of each of the C-terminal trypsin-digested peptides of the MS/MS spectra obtained from urine samples from lung adenocarcinoma patients and healthy individuals based on the statistical analysis, the relative ratio of the control specimen to the peak intensity was calculated, and comparison and evaluation were made between lung adenocarcinoma patients and healthy individuals. Mann-Whitney's U test was used as the assay method. For statistical analysis, JMP12 (SAS Institute Inc, Cary, N.C.) was used. The peak intensities of protein fragments in urine were compared between 85 cases with lung adenocarcinoma or 24 cases with early-stage lung adenocarcinoma and healthy individuals. The protein fragments satisfying the criteria that the ROC-AUC value was 0.6 or more or the p value was less than 0.1 were used as marker candidates. A total of 18 types of protein fragments were identified as lung adenocarcinoma diagnostic markers (Table 1) and a total of 13 types of protein fragments (Table 2) were identified as early-stage lung adenocarcinoma diagnostic markers.

TABLE 1

| Protein name | Protein abbreviation | Protein fragment sequence | Relative ratio to healthy individuals | Sensitivity (%) | Specificity (%) | ROC-AUC | p-value |
|---|---|---|---|---|---|---|---|
| A1AT fragment | | | | | | | |
| Alpha-1 antitrypsin | A1AT | GTEAAGAMF, SEQ ID NO: 11 | Undetected in healthy individuals | 35 | 100 | 0.68 | 0.0007 |
| AMBP fragment group | | | | | | | |
| Alpha-1-microglobulin/ bikunin precursor | AMBP | CVLFPYGG, SEQ ID NO: 12 | 2.34 | 71 | 76 | 0.78 | <0.0001 |
| Alpha-1-microglobulin/ bikunin precursor | AMBP | EYCGVPG, SEQ ID NO: 13 | 3.02 | 69 | 72 | 0.67 | 0.01 |
| Alpha-1-microglobulin/ bikunin precursor | AMBP | EYCGVPGDG, SEQ ID NO: 14 | 2.01 | 78 | 72 | 0.74 | 0.0003 |
| Alpha-1-microglobulin/ bikunin precursor | AMBP | EYCGVPGDGDE, SEQ ID NO: 15 | 2.09 | 58 | 92 | 0.7 | 0.0023 |
| Alpha-1-microglobulin/ bikunin precursor | AMBP | EYCGVPGDGDEE, SEQ ID NO: 16 | 13.01 | 39 | 92 | 0.65 | 0.0094 |
| Alpha-1-microglobulin/ bikunin precursor | AMBP | EYCGVPGDGDEEL, SEQ ID NO: 17 | 1.57 | 65 | 64 | 0.6 | 0.14 |
| Alpha-1-microglobulin/ bikunin precursor | AMBP | EYCGVPGDGDEELL, SEQ ID NO: 18 | 3 | 61 | 72 | 0.62 | 0.06 |
| Alpha-1-microglobulin/ bikunin precursor | AMBP | GECVPGEQEPEP, SEQ ID NO: 19 | 3.88 | 44 | 88 | 0.67 | 0.0037 |

TABLE 1-continued

| Protein name | Protein abbreviation | Protein fragment sequence | Relative ratio to healthy individuals | Sensitivity (%) | Specificity (%) | ROC-AUC | p-value |
|---|---|---|---|---|---|---|---|
| Alpha-1-microglobulin/bikunin precursor | AMBP | GECVPGEQEPEPILIP, SEQ ID NO: 20 | 1.86 | 74 | 72 | 0.76 | <0.0001 |
| CD59 fragment | | | | | | | |
| CD59 | CD59 | DLCNFNEQL, SEQ ID NO: 21 | 10.33 | 36 | 96 | 0.66 | 0.0022 |
| FINC fragment | | | | | | | |
| Fibronectin | FINC | FGFCPMA, SEQ ID NO: 22 | 1.42 | 59 | 68 | 0.64 | 0.03 |
| LMAN2 fragment | | | | | | | |
| Lectin, Mannose-Binding 2 | LMAN2 | LPTGYY, SEQ ID NO: 24 | 2.03 | 57 | 76 | 0.66 | 0.0112 |
| VASN fragment | | | | | | | |
| Vasorin | VASN | YLQGSSVQL, SEQ ID NO: 25 | 8.23 | 21 | 100 | 0.61 | 0.02 |
| WFDC2 fragment | | | | | | | |
| WAP Four-disulfide core domain protein 2 | WFDC2 | EGSCPQVNIN, SEQ ID NO: 26 | 4.99 | 43 | 80 | 0.61 | 0.068 |

TABLE 2

| Protein name | Protein abbreviation | Protein fragment sequence | Relative ratio to healthy individuals | Sensitivity (%) | Specificity (%) | ROC-AUC | p-value |
|---|---|---|---|---|---|---|---|
| AMBP fragment | | | | | | | |
| Alpha-1-microglobulin/bikunin precursor | AmBp | CVLFPYGG, SEQ ID NO: 12 | 1.79 | 58 | 76 | 0.7 | 0.0147 |
| Alpha-1-microglobulin/bikunin precursor | AmBp | EYCGVPG, SEQ ID NO: 13 | 5.31 | 66 | 76 | 0.68 | 0.0284 |
| Alpha-1-microglobulin/bikunin precursor | AmBp | EYCGVPGDG, SEQ ID NO: 14 | 1.52 | 70 | 82 | 0.69 | 0.0213 |
| Alpha-1-microglobulin/bikunin precursor | AmBp | EYCGVPGDGDE, SEQ ID NO: 15 | 1.44 | 54 | 92 | 0.66 | 0.0559 |
| Alpha-1-microglobulin/bikunin precursor | AmBp | EYCGVPGDGDEE, SEQ ID NO: 16 | 3.97 | 41 | 88 | 0.65 | 0.0327 |
| Alpha-1-microglobulin/bikunin precursor | AMBP | GECVPGEQEPEP, SEQ ID NO: 19 | 3.8 | 54 | 80 | 0.69 | 0.0078 |
| Alpha-1-microglobulin/bikunin precursor | AmBp | GECVPGEQEPEPILIP, SEQ ID NO: 20 | 2.01 | 79 | 72 | 0.79 | 0.0005 |
| CBPM fragment | | | | | | | |
| Membrane-bound carboxypeptidase M | CBPM | ENYNQYDLN, SEQ ID NO: 27 | 2.63 | 45 | 84 | 0.64 | 0.0384 |
| CD59 fragment | | | | | | | |
| CD59 | CD59 | DLCNFNEQL, SEQ ID NO: 21 | 8.75 | 25 | 96 | 0.61 | 0.0327 |

TABLE 2-continued

| Protein name | Protein abbre-viation | Protein fragment sequence | Relative ratio to healthy individuals | Sensi-tivity (%) | Speci-ficity (%) | ROC-AUC | p-value |
|---|---|---|---|---|---|---|---|
| DNAS1 fragment | | | | | | | |
| Deoxyribonuclease-1 | DNAS1 | GAVVPDSALPFNFQAAY, SEQ ID NO: 28 | 3.21 | 50 | 84 | 0.67 | 0.0144 |
| WFDC2 fragment | | | | | | | |
| WAP Four-disulfide core domain protein 2 | WFDC2 | EGSCPQVNINFPQLGL, SEQ ID NO: 29 | 5.66 | 33.3 | 96 | 0.63 | 0.049 |
| WISP2 fragment | | | | | | | |
| WNT1-inducible-signaling pathway protein 2 | WISP2 | GALCLLAEDDS, SEQ ID NO: 30 | 1.71 | 58 | 92 | 0.76 | 0.0018 |

[Example 4] Detection Method by Western Blotting

From the urine concentrated specimens (Example 2) of healthy individuals (7 persons) and lung adenocarcinoma patients (18 cases), the chondroitin sulfate chain equivalent to 2.5 µg of protein was removed from the proteins by chondroitinase ABC treatment (Sigma-Aldrich, Inc.). Then, the specimens were subjected to SDS-polyacrylamide gel electrophoresis using 5-20% polyacrylamide gel (DRC CO., LTD.). The proteins separated in the gel were transferred to a nitrocellulose membrane BA85 (GE Healthcare Japan Corporation), and the specific antibody recognizing the C-terminal amino acid sequence of the protein fragment EYCGVPGDGDEEL (SEQ ID NO: 17) derived from α-1-microglobulin/bikunin precursor was used to visualize the protein fragments having the C-terminal amino acid sequence of EYCGVPGDDEEL (SEQ ID NO: 33) (FIG. 1A). Further, the commercially available antibody (AMBP antibody, Product No. GTX101069, GeneTex, Inc.) recognizing α-1-microglobulin/bikunin precursor was used to visualize the abundance of α-1-microglobulin/bikunin precursor protein present in urine (FIG. 1B). Each band was visualized by obtaining a chemiluminescent signal from a horseradish peroxidase-labeled secondary antibody with a cooled CCD camera (Fujifilm Holdings Corporation), and the band was quantified using image analysis software ImageJ (National Institutes of Health (NIH)). The relative abundance of α-1-microglobulin/bikunin precursor protein and protein fragment having a C-terminal amino acid sequence of EYCGVPGDDEEL (SEQ ID NO: 33) in each sample was plotted (FIG. 1(C)). In this experiment, 1 out of 7 healthy individual specimens and 13 out of 18 lung adenocarcinoma patient specimens were found in which the amount of the detected C-terminus was twice or more higher than the average of healthy individuals. Note that, in FIGS. 1(A) to 1 (C), electrophoresis photographs on the left side and graphs 1 to 3 are from healthy persons, and graphs 4 to 13 are from the specimens of lung adenocarcinoma patients. In FIGS. 1(A) to (C), electrophoresis photographs on the right side and graphs 1 to 4 are from healthy persons, and graphs 5 to 12 are from the specimens of lung adenocarcinoma patients.

[Example 5] Evaluation Method of Lung Adenocarcinoma

Figure 2:
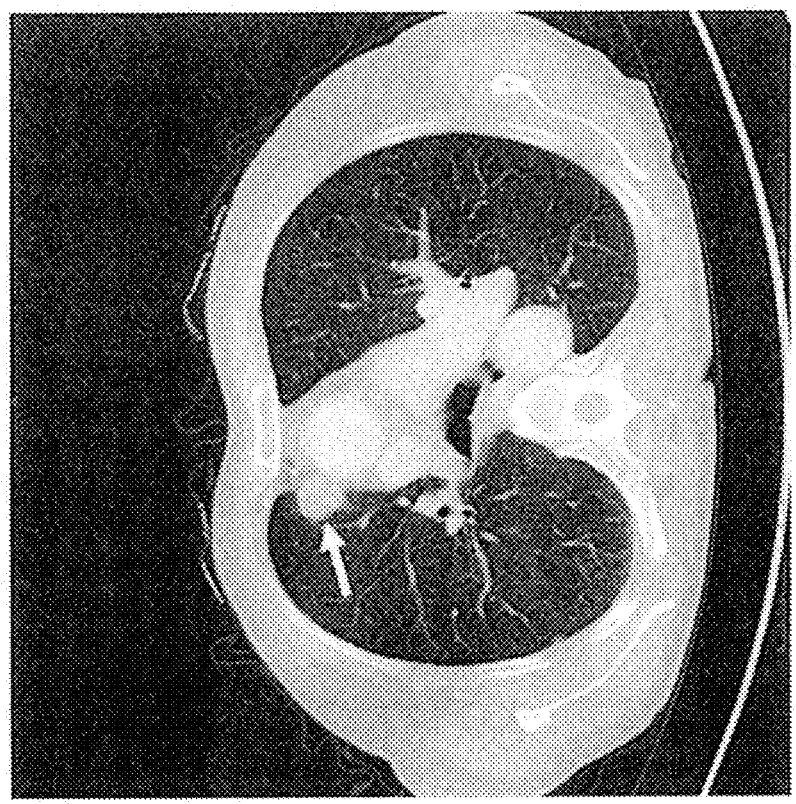
FIG. 2 is a view showing a chest CT image in the lung adenocarcinoma case in which a protein fragment having a C-terminal amino acid sequence of EYCGVPGDGDEEL (SEQ ID NO: 17) has been found at a high level by in vitro treatment of a test subject-derived sample (urine). A 2 cm primary lesion is recognized on the mediastinum side of the right upper lobe S3.
Figure 3:
FIG. 3 is a view showing a chest PET-CT image in the lung adenocarcinoma case in which a protein fragment having a C-terminal amino acid sequence of EYCGVPGDGDEEL (SEQ ID NO: 17) has been found at a high level by in vitro treatment of a test subject-derived sample (urine). Abnormal accumulation of PET is recognized in a 2 cm primary lesion, located on the mediastinum side of the right upper lobe S3.
Figure 4:
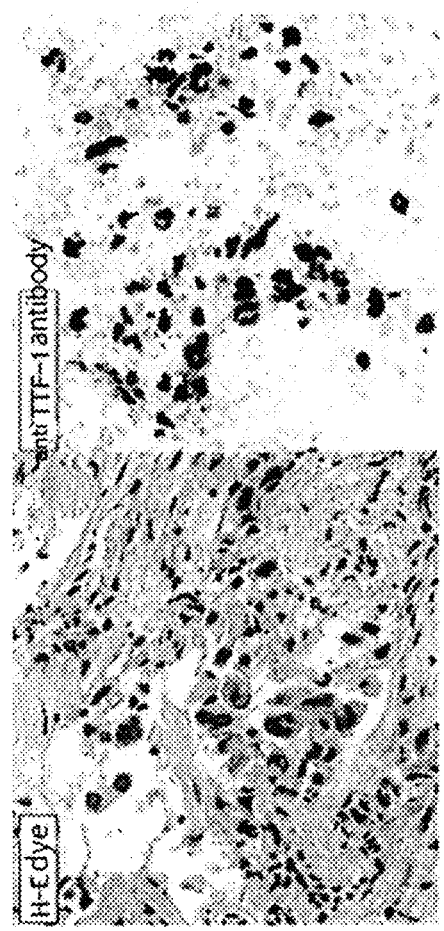
FIG. 4 shows images of the lung adenocarcinoma tissue collected by transbronchial biopsy (H-E staining and chemiluminescence of the immune tissue using an anti-TTF-1 antibody) in the case with lung adenocarcinoma in which a protein fragment having a C-terminal amino acid sequence of EYCGVPGDGDEEL (SEQ ID NO: 17) has been found at a high level by in vitro treatment of a test subject-derived sample (urine).

Among patients with pulmonary nodule shadows or tumor shadows, suspected of primary lung cancer by chest image examination, lung adenocarcinoma diagnosis was performed by tissue diagnosis such as surgery, lung biopsy, lymph node biopsy or bone biopsy or by cytological diagnosis of expectoration, pleural effusion, and the like. The clinical stage of lung adenocarcinoma was determined using the intensity of accumulation by PET-CT examination, image examination by head MRI examination and chest CT examination, bone biopsy, cytological diagnosis by lymph node puncture or pleural effusion cytology examination. In the lung adenocarcinoma cases in which the protein fragment having a C-terminal amino acid sequence of EYCGVPGDGDEEL (SEQ ID NO: 17), derived from α-1-microglobulin/bikunin precursor in urine showed a high value in Example 2, a 2 cm large nodule shadow was observed at the right upper lobe in the chest CT examination (FIG. 2), and abnormal accumulation was observed in the same site in PET-CT examination (FIG. 3). Lung adenocarcinoma positive for thyroid transcription factor-1 (TTF-1) was detected from the tissue obtained by transbronchial biopsy (FIG. 4). In this case, the area of the spectrum of the protein fragment having the C-terminal amino acid sequence of EYCGVPGDGDEEL (SEQ ID NO: 17), derived from α-1-microglobulin/bikunin precursor, was 2.1 times the average value of healthy individuals.

[Example 6] Comparison of Utility with CEA in Diagnosis of Early-Stage Lung Adenocarcinoma The utility of CEA and protein fragments in urine was compared among 14 cases where blood CEA levels could be confirmed, among 24 cases diagnosed as early-stage lung adenocarcinoma (Example 1). For example, when the amount of the protein fragment having the C-terminal sequence of CVLFPYGG, SEQ ID NO: 12, derived from α-1-microglobulin/bikunin precursor, was 1.25 times the average value of healthy individuals in Example 2 and this case was judged to be positive, 11 out of 14 cases with early-stage lung adenocarcinoma could be judged to be positive. Meanwhile, when the reference value of blood CEA level was 5.0 ng/ml, only 4 out of 14 cases with early-stage lung adenocarcinoma were positive.

[Example 7] Screening

Specimens were prepared in the same manner as in Example 2, and patients with adenocarcinoma were screened by subjecting the patients to MRM. Urine samples (~50 mL) were collected. Then, the pretreatment and the acquisition and analysis of analytical data were performed. Specifically, in the pretreatment, the urine samples were concentrated to 200 to 250-folds using Amicon Ultra-15 (10 kDa molecular weight cut-off) and Amicon Ultra-4 (10 kDa molecular weight cut-off) (Merck KGaA). The low molecular weight molecules were removed by washing, and then concentrated specimens were obtained. The proteins in the concentrated specimens were quantified. The concentrations of all the specimens were adjusted to 10 mg/mL of total protein using a buffer solution and the resulting specimens were used in the subsequent analysis step. Subsequently, the samples were digested with trypsin in a buffer after reductive alkylation. After desalting and purification, trypsin-digested peptides derived from protein fragments were fractionated by ion exchange chromatography (LC column: PolySUL-FOETHYL A™ (PolyLC Inc. USA), with an inner diameter of 4.6 mm and a length of 50 mm; flow rate: 0.4 mL/min; solvent: a solution of 20% acetonitrile/phosphoric acid (pH 2.55), with respect to the solvent, the concentration of a solution of 20% acetonitrile/5 mM monopotassium phosphate and 0.5M NaCl (pH 2.55) was stepwise increased (0 to 100%) for separation), and a trypsin-digested peptide mixture containing the C-terminal peptide of the protein fragment was obtained. Each of the samples thus obtained was separately subjected to a high performance liquid chromatography/triple quadrupole mass spectrometer (QTRAP® 5500 System (AB Sciex.)), and quantification of the peptides was performed by Multiple Reaction Monitoring (MRM), simultaneously with separation of the mixture. The fragmentation rate ($F_n$) of each protein was obtained by the following calculation formula, and the patient sample whose fragmentation rate was 1.5 times higher than the average value of the healthy individual group was judged to be positive.

$$\text{Protein fragmentation rate } (F_n) = C_n / I_n \quad \text{[Equation 1]}$$

$C_n$: amount of each protein fragment (amount of peptide in the protein fragment sequence in Table 3)

$I_n$: amount of the original protein derived from each protein fragment $$\text{Relative ratio } (R_n) \text{ of protein fragmentation rates between patient and healthy individual} = F_p / F_h \quad \text{[Equation 2]}$$

$F_p$: protein fragmentation rate of patient sample $F_h$: average value of protein fragmentation rates of healthy individual group The amount of the original protein in $I_n$ refers to an amount of a trypsin-digested peptide commonly included in a protein fragment or full-length protein. Here, the following internal sequences were respectively used.

AMBP: TVAACNLPIVR (at positions 283 to 293 of SEQ ID NO: 2 in the sequence listing)

WFDC2: CCSAGCATFCSLPNDK (at positions 61 to 76 of SEQ ID NO: 7 in the sequence listing)

WISP2: CPLGVPLVLDGCGCCR (at positions 39 to 54 of SEQ ID NO: 10 in the sequence listing)

Urine specimens of 28 cases with early-stage lung adenocarcinoma (clinical stage IA: 19 cases, IB: 7 cases, IIA: 1 case, IIB: 1 case) and 40 healthy individuals were subjected to MRM, whereby the fragmentation rate of each protein was compared between cases with early-stage lung adenocarcinoma and healthy individuals. The protein fragments satisfying the criteria that the ROC-AUC value was 0.6 or more or the p value was less than 0.1 were used as early-stage lung adenocarcinoma diagnostic markers. A total of 12 types (Table 3) were identified as early-stage lung adenocarcinoma diagnostic markers by this analysis.

Urine specimens of 28 cases with early-stage lung adenocarcinoma and 40 healthy individuals were subjected to MRM, and the fragmentation rate of the protein fragment having the C-terminal amino acid sequence of EYCGVPGDGDEE (SEQ ID NO: 16), derived from α-1-microglobulin/bikunin precursor, was measured. When the patient sample whose fragmentation rate was 1.5 times or more higher than the average value of the healthy individual group was defined as positive, 7 healthy individuals were positive, and 17 cases with early-stage lung adenocarcinoma were positive. When the fragmentation rate as a reference value was 2.18 times the average value of the healthy individual group, 1 healthy individual was positive and 16 cases with early-stage lung adenocarcinoma were positive. Based on the reference value, the sensitivity was 57.1%, the specificity was 97.5%, and the ROC-AUC value was 0.819.

Separately, urine specimens of 28 cases with early-stage lung adenocarcinoma and 40 healthy individuals were subjected to MRM, and the fragmentation rate of the protein fragment having the C-terminal amino acid sequence of EGSCPQVNINFPQLG (SEQ ID NO: 23) in WAP four-disulfide core domain protein 2 was measured. When the patient sample whose fragmentation rate was 1.5 times or more higher than the average value of the healthy individual group was defined as positive, 3 healthy individuals were positive, and 16 cases with early-stage lung adenocarcinoma were positive. Based on the reference value, the sensitivity was 69.6%, the specificity was 91.4%, and the ROC-AUC value was 0.855.

TABLE 3

| Protein name | Protein Abbreviation | Protein fragment sequence | Fragmentation rate of lung adenocarcinoma group | Fragmentation rate of healthy individual group | Relative ratio to healthy individuals | sensitivity % | Specificity % | ROC-AUC | p-value |
|---|---|---|---|---|---|---|---|---|---|
| AMBP fragment group | | | | | | | | | |
| Alpha-1-microglobulin/bibikunin precursor | AMBP | CVLFPYGG, SEQ ID NO: 12 | 0.033 | 0.018 | 1.8 | 42.9 | 85 | 0.615 | 0.108 |
| Alpha-1-microglobulin/bibikunin precursor | AMBP | EYCGVPGD, SEQ ID NO: 31 | 0.052 | 0.022 | 2.4 | 55.6 | 87.2 | 0.71 | 0.0039 |

TABLE 3-continued

| Protein name | Protein Abbreviation | Protein fragment sequence | Fragmentation rate of lung adenocarcinoma group | Fragmentation rate of healthy individual group | Relative ratio to healthy individuals | sensitivity % | Specificity % | ROC-AUC | p-value |
|---|---|---|---|---|---|---|---|---|---|
| Alpha-1-microglobulin/bibikunin precursor | AMBP | EYCGVPGDG, SEQ ID NO: 14 | 0.070 | 0.031 | 2.3 | 50 | 85 | 0.6574 | 0.0311 |
| Alpha-1-microglobulin/bibikunin precursor | AMBP | EYCGVPGDGDE, SEQ ID NO: 15 | 0.061 | 0.028 | 2.2 | 67.9 | 65 | 0.68 | 0.0118 |
| Alpha-1-microglobulin/bibikunin precursor | AMBP | EYCGVPGDGDEE, SEQ ID NO: 16 | 0.067 | 0.019 | 3.5 | 57.1 | 97.5 | 0.819 | <0.001 |
| Alpha-1-microglobulin/bibikunin precursor | AMBP | EYCGVPGDGDEEL, SEQ ID NO: 17 | 0.570 | 0.370 | 1.5 | 67.9 | 62.5 | 0.667 | 0.0198 |
| Alpha-1-microglobulin/bibikunin precursor | AMBP | EYCGVPGDGDEELL, SEQ ID NO: 18 | 3.100 | 0.720 | 4.3 | 71.4 | 65 | 0.695 | 0.0066 |
| Alpha-1-microglobulin/bibikunin precursor | AMBP | GECVPGEQEPE, SEQ ID NO: 32 | 0.023 | 0.018 | 1.3 | 57.1 | 72.5 | 0.654 | 0.0219 |
| Alpha-1-microglobulin/bibikunin precursor | AMBP | GECVPGEQEPEP, SEQ ID NO: 19 | 0.130 | 0.099 | 1.3 | 78.6 | 55 | 0.65 | 0.0363 |
| WFDC2 fragment | | | | | | | | | |
| WAP Four-Disulfide Core Domain 2 | WFDC2 | EGSCPQVNIN, SEQ ID NO: 26 | 0.037 | 0.019 | 1.9 | 70.8 | 81.8 | 0.812 | <0.001 |
| WAP Four-Disulfide Core Domain 2 | WFDC2 | EGSCPQVN1NFPQLG, SEQ ID NO: 34 | 0.025 | 0.012 | 2.1 | 69.6 | 91.4 | 0.855 | <0.001 |
| WI5P2 fragment | | | | | | | | | |
| WNT1-inducible-signaling pathway protein 2 | WISP | GALCLLAEDDS, SEQ ID NO: 30 | 7.300 | 3.600 | 2.0 | 85.2 | 53 | 0.68 | 0.0159 |

Further, a logistic regression model predicting early-stage lung adenocarcinoma was produced using a total of 12 protein fragments listed in Table 3. From the 12 protein fragments, (1) a protein fragment (X) having the C-terminal sequence of EYCGVPGDGDEE (SEQ ID NO: 16), derived from α-1-microglobulin/bikunin precursor and (2) a protein fragment (Y) having the C-terminal sequence of EGSCPQVNINFPQLG (SEQ ID NO: 23), derived from WAP four-disulfide core domain protein 2 were selected as explanatory variables to be used for the logistic regression model, using the stepwise variable selection method. In the stepwise variable selection method, the criteria for adding and removing variables was p value=0.2.

The logistic regression equation obtained as a result of this procedure is as follows:

$$\text{Logit}(p) = 6.7597953165 - 92.29827738 \times X - 248.897852 \times Y \qquad \text{[Equation 3]}$$

Multiple logistic regression analysis was performed using JMP 12 (SAS Institute Inc, Cary, N.C.), and each coefficient of the regression equation was calculated using data of specimens of 35 healthy individuals and 23 cases with early-stage lung adenocarcinoma.

Predicted values in each urine sample were calculated using the regression equation. When a predicted value of 0.5358 was used as a cutoff value, the sensitivity was 82.6%, the specificity was 94.3%, and the ROC-AUC value was 0.901 based on the reference value.

[Example 8] Detection Method by Western Blotting of AMBP

Figure 5:
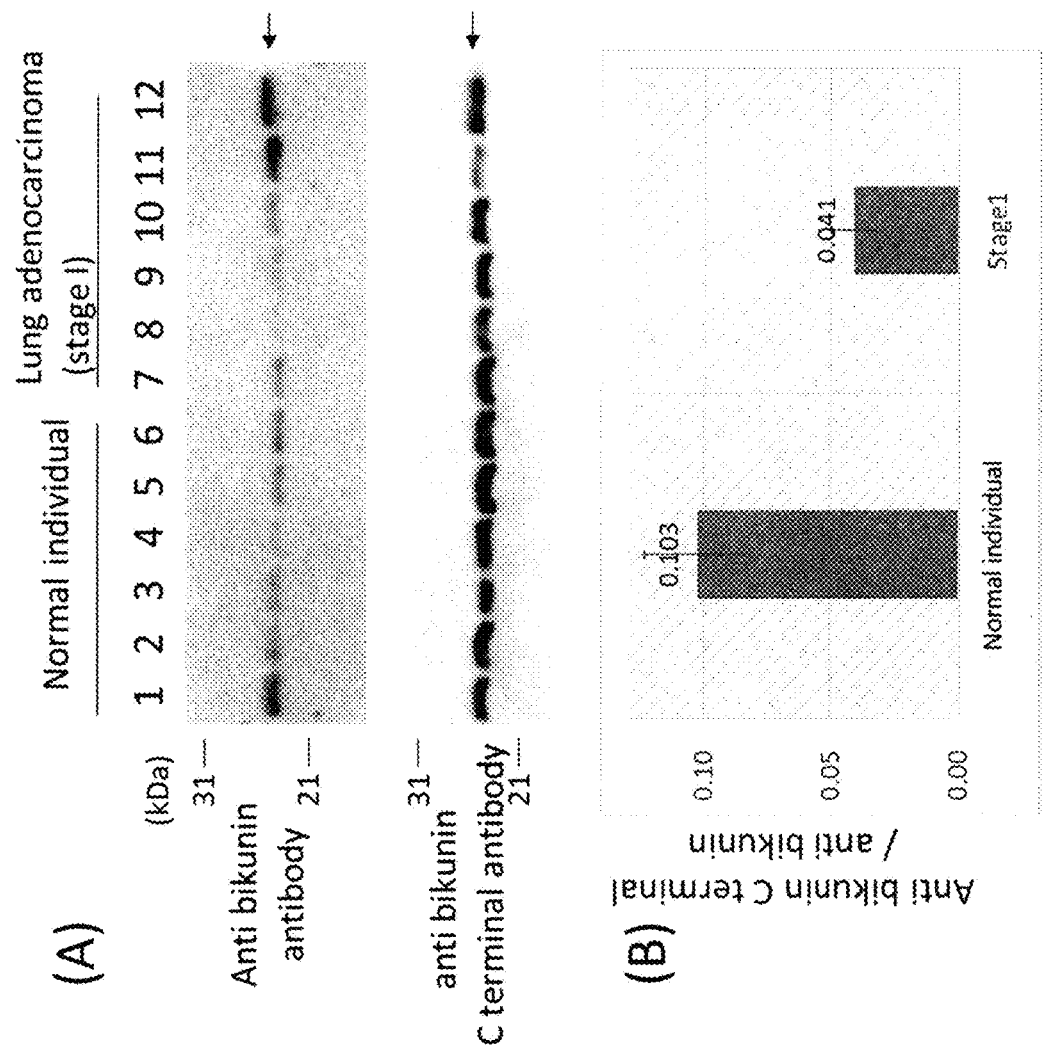
FIG. 5(A) is a view showing the result of western blotting performed on urine samples using a commercially available anti-bikunin antibody and an antibody recognizing the normal structure (C-terminus) of bikunin.
FIG. 5(B) is a graph in which the amounts of proteins having a normal structure (C-terminus) in urine samples of healthy individuals and adenocarcinoma patients.

Concentrated urine specimens of healthy individuals (9 persons) and lung adenocarcinoma patients (9 cases) were obtained in the same manner as in Example 2. The chondroitin sulfate chain equivalent to 2.5 μg of protein was removed from the proteins by chondroitinase ABC treatment (Sigma-Aldrich, Inc.). Then, the specimens were subjected to SDS-polyacrylamide gel electrophoresis using 5-20% polyacrylamide gel (DRC CO., LTD.). The proteins separated in the gel were transferred to a nitrocellulose membrane BA85 (GE Healthcare Japan Corporation), and the specific antibody recognizing the C-terminal amino acid sequence RFSN (SEQ ID NO: 35) of the normal protein derived from α-1-microglobulin/bikunin precursor was used to visualize the normal (full-length) protein having the C-terminal amino acid sequence of RFSN (SEQ ID NO: 35) (FIG. 5A; anti-bikunin C-terminal antibody). Further, the commercially available antibody (AMBP antibody, Product No. GTX101069, GeneTex, Inc.) recognizing α-1-microglobulin/bikunin precursor was used to visualize the abundance of α-1-microglobulin/bikunin precursor protein present in urine (FIG. 5A; anti-bikunin antibody). Each band was visualized by obtaining a chemiluminescent signal from a horseradish peroxidase-labeled secondary antibody with a digital camera (Canon Inc.), and the band was quantified using image analysis software ImageJ (National Institutes of Health (NIH)). The relative abundance of α-1-microglobulin/bikunin precursor protein and normal protein having a C-terminal amino acid sequence of RFSN (SEQ ID NO: 35) in each sample was plotted (FIG. 5(B)). In this experiment, 6 out of 9 lung adenocarcinoma patient specimens were found in which the ratio of the detected total length was ½ or less lower than the average of healthy individuals. Note that, in FIGS. 5(A) and 5(B), lanes 1 to 6 are samples derived from healthy persons, and lanes 7 to 12 are samples derived from stage I lung adenocarcinoma patients.

[Example 9] Detection of Cleavage of WFDC2

Specimens were prepared in the same manner as in Example 2, and patients with adenocarcinoma were screened by subjecting the patients to MRM. Urine samples (~50 mL) were collected. Then, the pretreatment and the acquisition and analysis of analytical data were performed. Specifically, in the pretreatment, the urine samples were concentrated to 200 to 250-folds using Amicon Ultra-15 (10 kDa molecular weight cut-off) and Amicon Ultra-4 (10 kDa molecular weight cut-off) (Merck KGaA). The low molecular weight molecules were removed by washing, and then concentrated specimens were obtained. The proteins in the concentrated specimens were quantified. The concentrations of all the specimens were adjusted to 10 mg/mL of total protein using a buffer solution and the resulting specimens were used in the subsequent analysis step. Subsequently, the samples were digested with trypsin in a buffer after reductive alkylation. After desalting and purification, trypsin-digested peptides derived from protein fragments were fractionated by ion exchange chromatography (LC column: PolySULFOETHYL A™ (PolyLC Inc. USA), with an inner diameter of 4.6 mm and a length of 50 mm; flow rate: 0.4 mL/min; solvent: a solution of 20% acetonitrile/phosphoric acid (pH 2.55), with respect to the solvent, the concentration of a solution of 20% acetonitrile/5 mM monopotassium phosphate and 0.5M NaCl (pH 2.55) was stepwise increased (0 to 100%) for separation), and a trypsin-digested peptide mixture containing the C-terminal peptide of the protein fragment was obtained.

Each of the samples thus obtained was separately subjected to a high performance liquid chromatography/triple quadrupole mass spectrometer (QTRAP® 5500 System (AB Sciex.)), and quantification of the peptides was performed by Multiple Reaction Monitoring (MRM), simultaneously with separation of the mixture.

Figure 6:
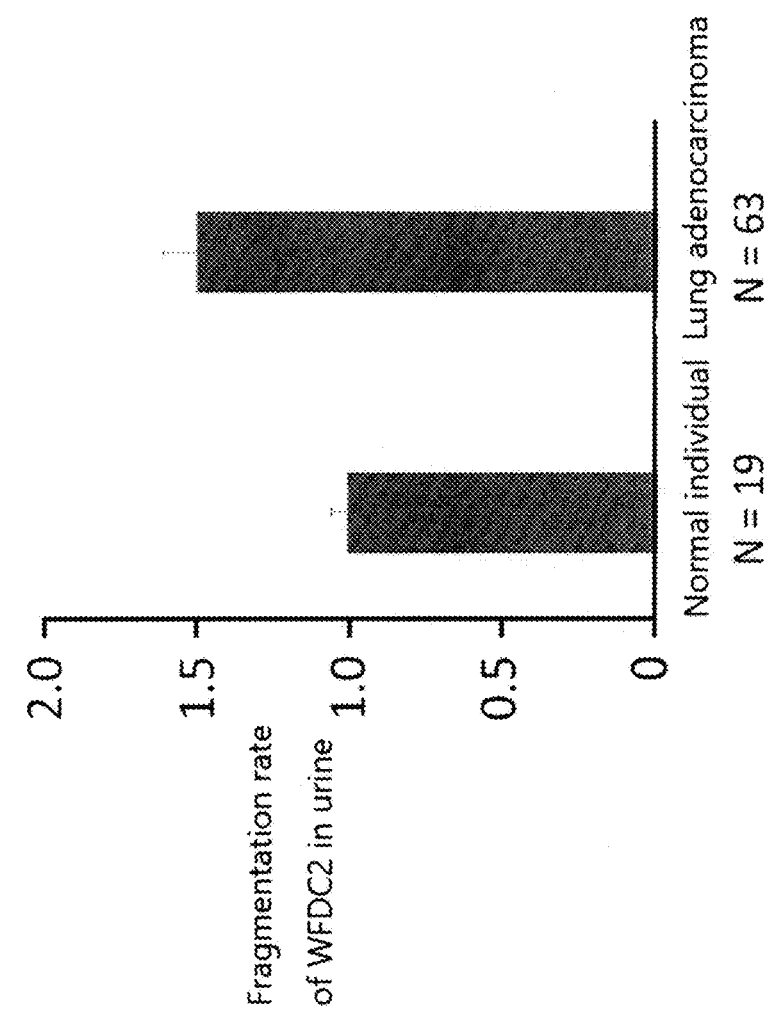
FIG. 6 is a graph showing the fragmentation rate of WFDC2 after in vitro treatment of test subject-derived samples (urine) from healthy individuals and adenocarcinoma patients.

Urine specimens of 63 cases with early-stage lung adenocarcinoma (clinical stage IA: 42 cases, IB: 16 cases, IIA: 2 cases, IIB: 3 cases) and 19 healthy individuals were subjected to MRM. The fragmentation rate of the protein fragment of WFDC2 between early-stage lung adenocarcinoma patients and healthy individuals was determined, and graphed by setting the average value of the healthy individual group to 1 (FIG. 6). The fragmentation rate of WFDC2 was measured using trypsin-digested peptides having the amino acid sequence EGSCPQVNINFPQLGL (SEQ ID NO: 29).

When the patient sample whose fragmentation rate (expressed by the relative ratio) was 1.3 times or more higher than the average value of the healthy individual group was defined as positive, 1 healthy individual was positive, and 26 cases with early-stage lung adenocarcinoma were positive. Based on the reference value, the sensitivity was 41.2%, the specificity was 94.7%, and the ROC-AUC value was 0.723.

Figure 7:
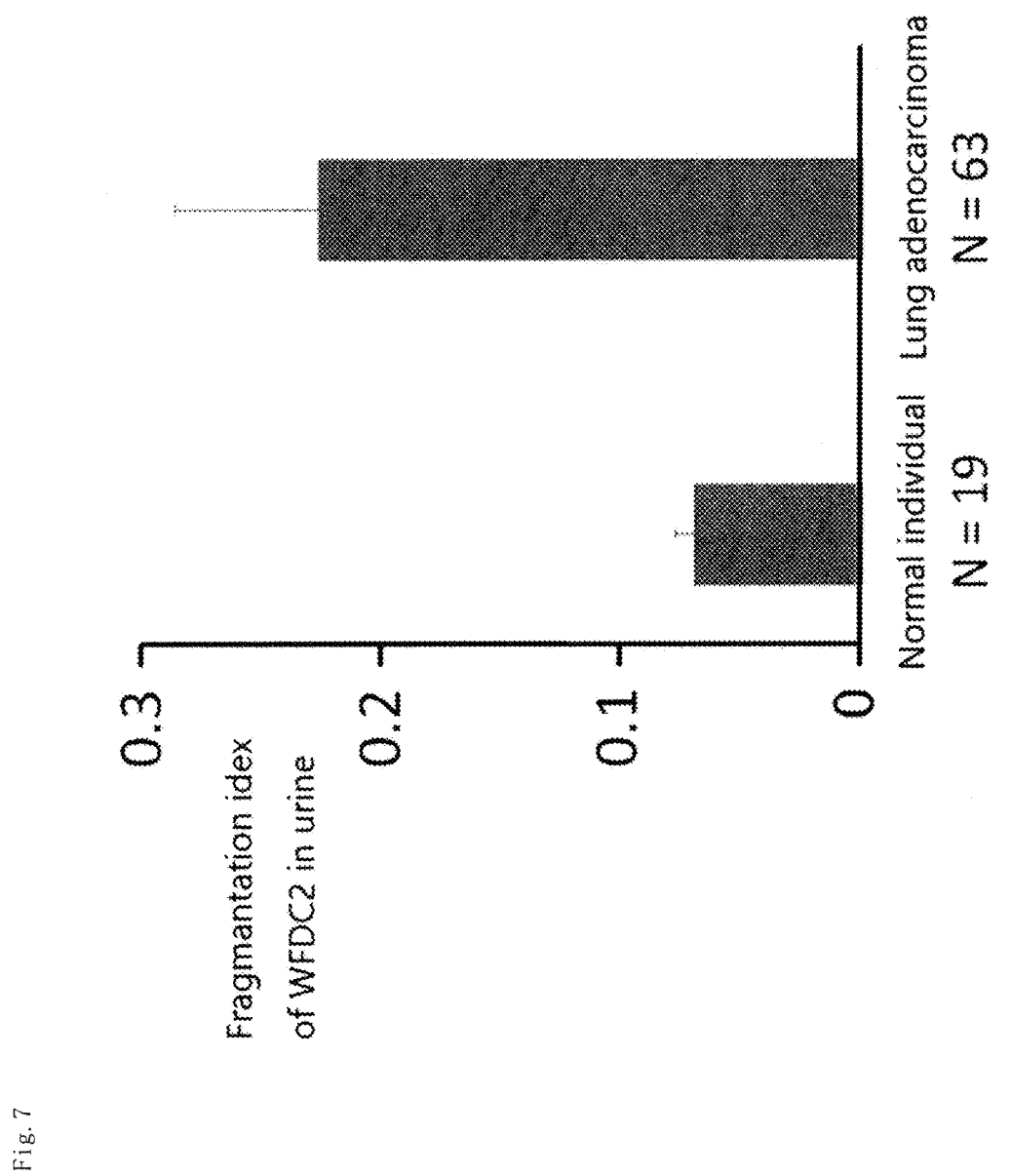
FIG. 7 is a diagram showing the fragmentation index of WFDC2 after in vitro treatment of test subject samples (urine) of healthy individuals and adenocarcinoma patients.

In order to efficiently detect the cleavage of WFDC2, the fragment index (Ei) of WFDC2 was calculated by the following calculation formula, using (A) the fragmentation rate of trypsin-digested peptides having the amino acid sequence EGSCPQVNINFPQLGL (SEQ ID NO: 29) and (B) the abundance of the protein fragment having the C-terminal amino acid sequence of EGSCPQVNIN (SEQ ID NO: 26). The patient sample whose fragmentation index was 1.3 times or more higher than the average value of the healthy individual group was defined as positive. (FIG. 7)

$$\text{Fragmentation index } (Ei) = B/A \qquad \text{[Equation 4]}$$

Example 10

Urine specimens of 63 cases with early-stage lung adenocarcinoma used in Example 9 (clinical stage IA: 42 cases, IB: 16 cases, IIA: 2 cases, IIB: 3 cases) and 19 healthy individuals were subjected to MRM, and the fragmentation index of WFDC2 was determined. When the patient sample whose fragmentation index was 1.3 times or more higher than the average value of the healthy individuals was defined as positive, 5 healthy individuals were positive, and 52 cases with early-stage lung adenocarcinoma were positive. Based on the reference value, the sensitivity was 82.5%, the specificity was 73.7%, and the ROC-AUC value was 0.882.

Example 11

The amount equivalent to 20 μg of the proteins extracted from a normal human airway epithelial cell line (BEAS-2B) and human adenocarcinoma cell lines (lung adenocarcinoma: Ad-1, HLC-1, PC-9, gastric adenocarcinoma: MKN-45, KatoIll, MKN-7, pancreatic cancer: T3M4, breast adenocarcinoma: MCF7) was subjected to SDS polyacrylamide gel electrophoresis using Miniprothian TGX gel (Bio-Rad Laboratories, Inc.). The proteins separated in the gel were transferred to an Immobilon-P membrane (Merck KGaA) and the specific antibody recognizing the C-terminal part of the protein fragment having the C-terminal amino acid sequence of EYCGVPGDGDEEL (SEQ ID NO: 17), derived from α-1-microglobulin/bikunin precursor, was used to visualize the protein fragments having the C-terminal amino acid sequence of EYCGVPGDGDEEL (SEQ ID NO: 17) (FIG. 8(A)). Further, the abundance in cell lysates derived from the cell lines was visualized using a commercially available antibody (AMBP antibody, Product No. GTX101069, GeneTex, Inc.) recognizing the bikunin portion of α-1-microglobulin/bikunin precursor (FIG. 8(B)). To visualize each band, a chemiluminescent signal from a horseradish peroxidase-labeled secondary antibody was obtained with Fusion FX7 (Vilber-Lourmat) and the band was quantified. The relative abundance of α-1-microglobulin/bikunin precursor protein and protein fragment having the C-terminal amino acid sequence of EYCGVPGDGDEEL (SEQ ID NO: 17) in each sample was plotted (FIG. 8(C)). In this experiment, Ad-1, HLC-1, PC-9, MKN-45, KatoIII, MKN-7, T3M4, and MCF7 were found in which the amount of the detected C-terminus was 1.25 times or more higher than the amount of the normal human airway epithelial cell line.

Figure 8:
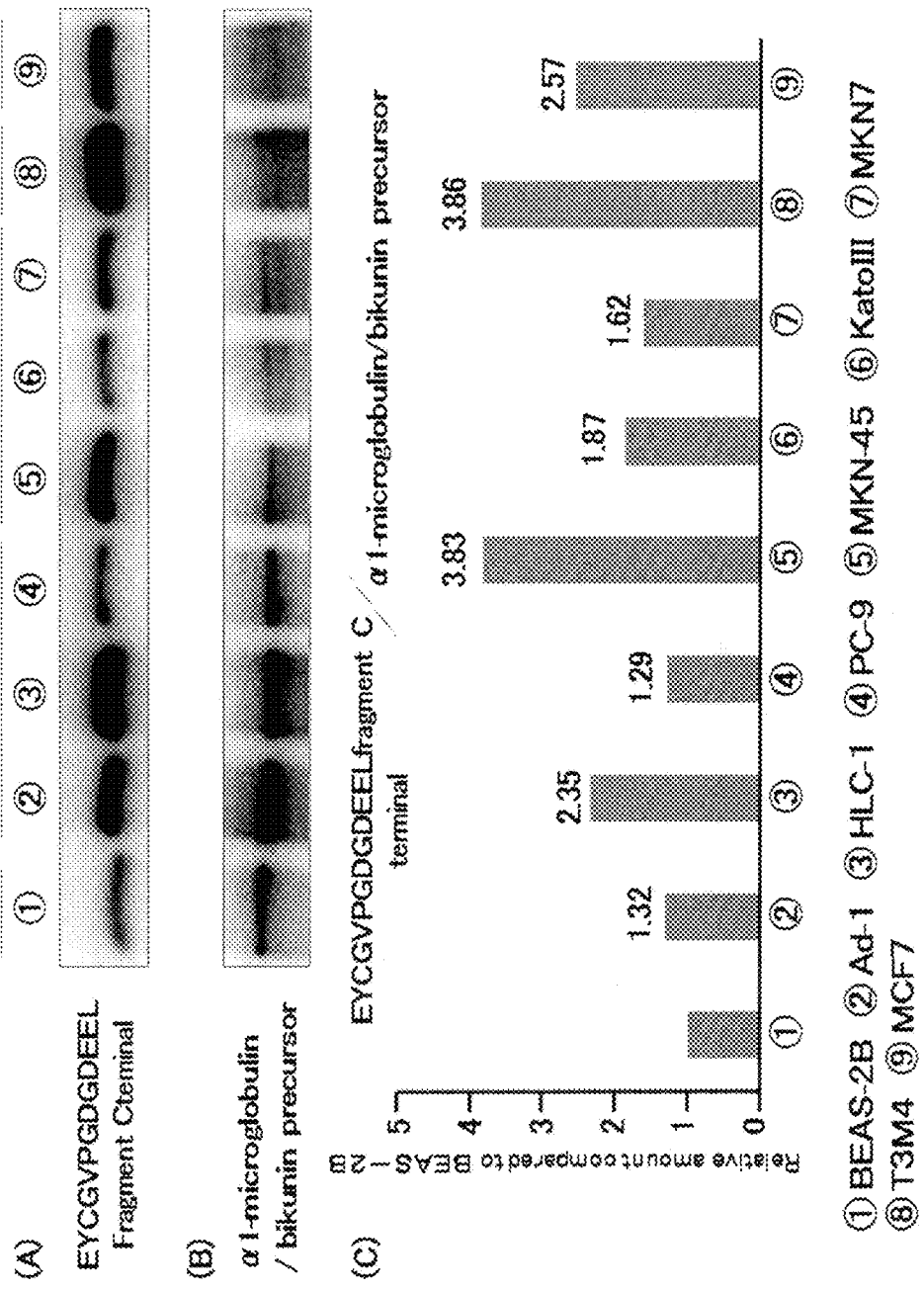
FIG. 8(A) is a diagram visualizing protein fragments having a C-terminal amino acid sequence of EYCGVPGDGDEEL (SEQ ID NO: 17).
FIG. 8(B) is a diagram visualizing the abundance of the bikunin moiety of α-1-microglobulin/bikunin precursor in cell lysates derived from cells or cell lines.
FIG. 8(C) is a diagram of plotting the relative abundance of α-1-microglobulin/bikunin precursor protein and protein fragment having a C-terminal amino acid sequence of EYCGVPGDGDEEL (SEQ ID NO: 17) in samples.

In FIG. 8, the specimens with respective numbers are as follows:

| | |
|---|---|
| 1: BEAS-2B | (Normal human airway epithelial cells) |
| 2: Ad-1 | (Lung adenocarcinoma) |
| 3: HLC-1 | (Lung adenocarcinoma) |
| 4: PC-9 | (Lung adenocarcinoma) |
| 5: MKN-45 | (Gastric adenocarcinoma) |
| 6: KatoIII | (Gastric adenocarcinoma) |
| 7: MKN7 | (Gastric adenocarcinoma) |
| 8: T3M4 | (Pancreatic cancer) |
| 9: MCF7 | (Breast cancer) |

Example 12

Figure 9:
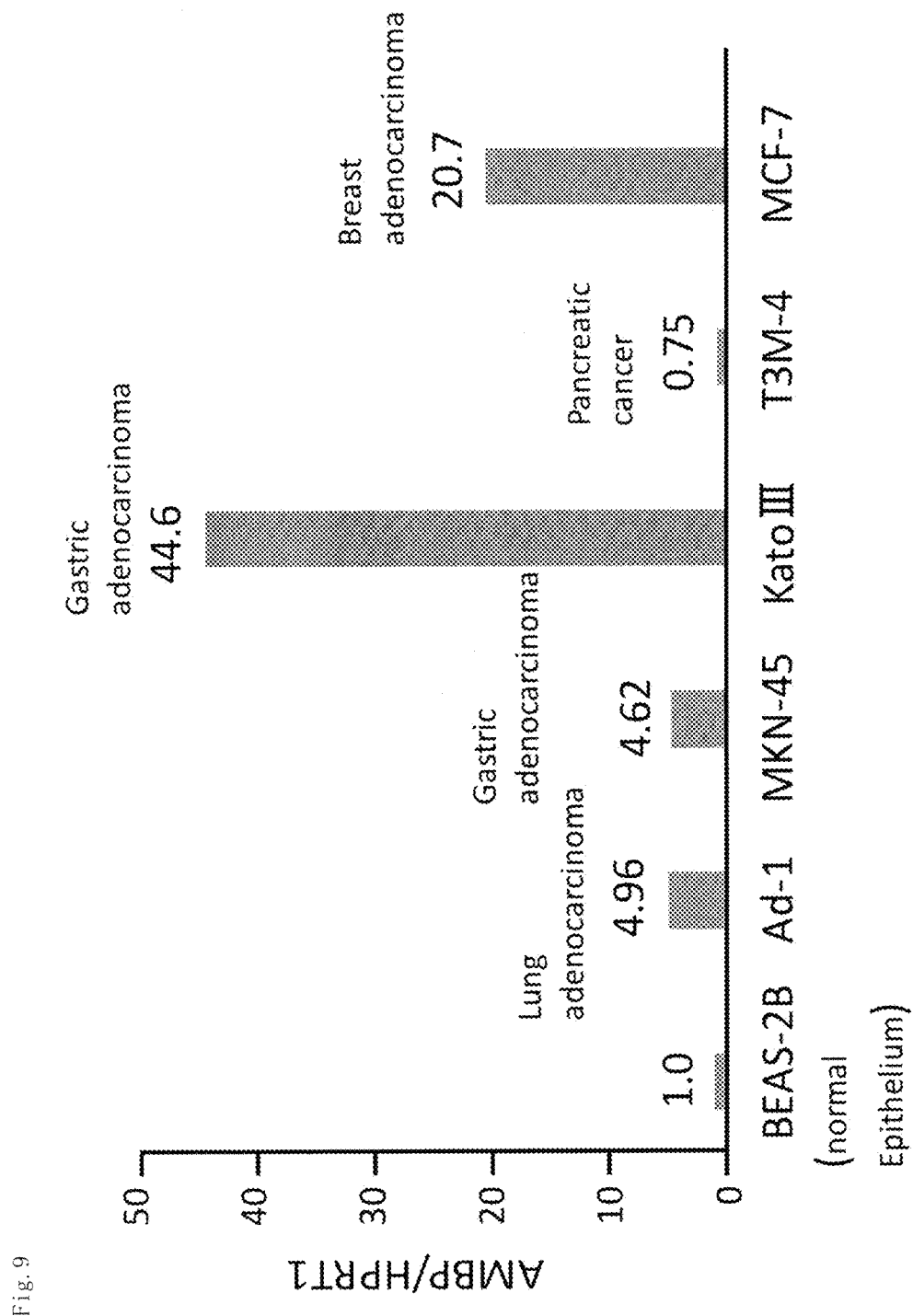
FIG. 9 is a diagram showing the expression of AMBP in human adenocarcinoma cell lines.
Figure 10:
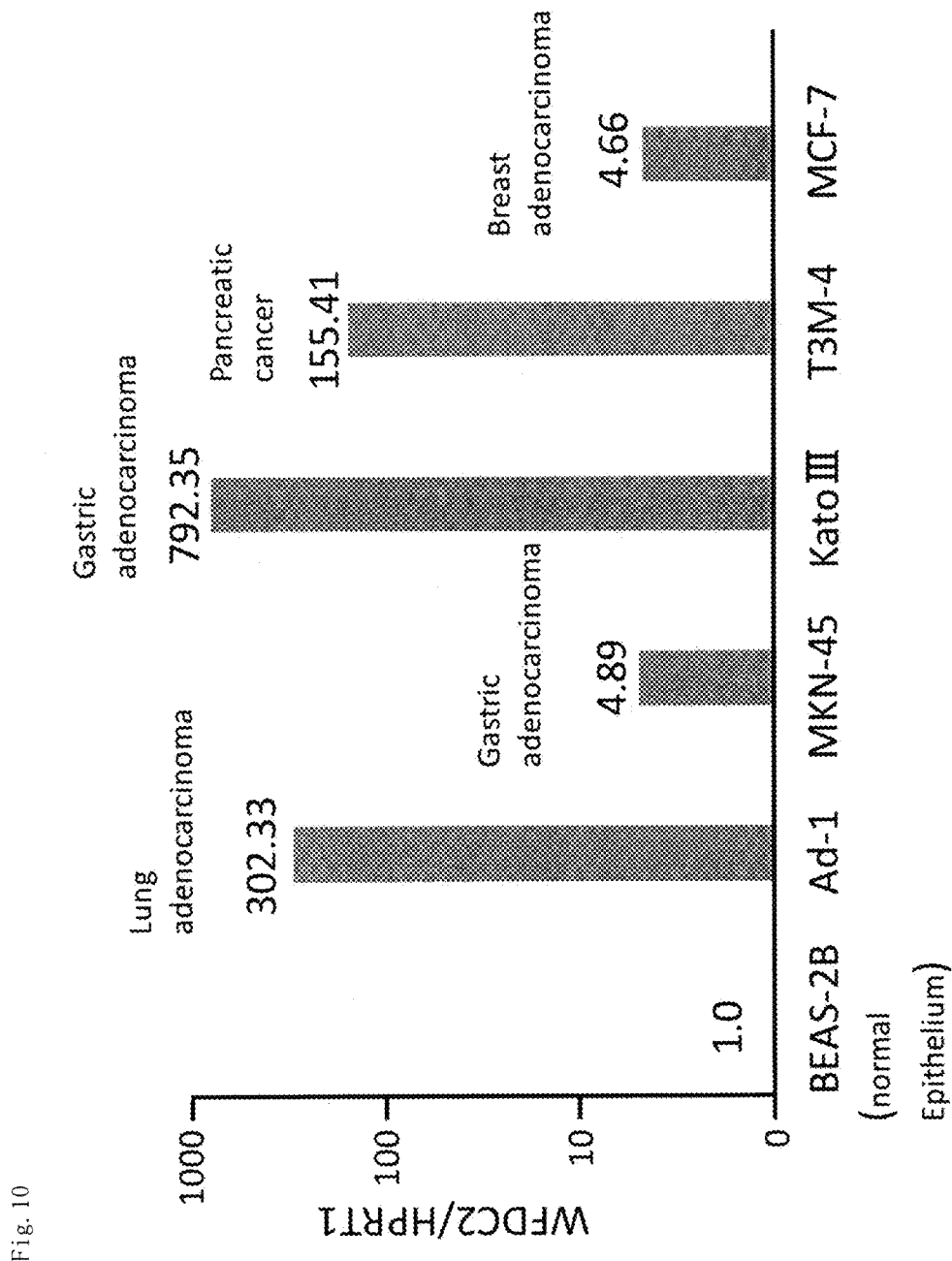
FIG. 10 is a diagram showing the expression of WFDC2 in human adenocarcinoma cell lines.

RNAs were extracted from a normal human airway epithelial cell line (BEAS-2B) and human adenocarcinoma cell lines (lung adenocarcinoma: Ad-1, gastric adenocarcinoma: MKN-45, KatoIII, pancreatic cancer: T3M4, breast adenocarcinoma: MCF7), using a RiboPure RNA Purification Kit (Thermo Fisher Scientific Inc.). cDNAs were synthesized in an amount corresponding to 500 ng of RNAs derived from each sample using a High-Capacity RNA-to-cDNA Kit (Thermo Fisher Scientific Inc.). The synthesized cDNAs were subjected to quantitative PCR using a primer & probe set (Assay ID: Hs00155697_m1, Hs00196109_m1, Hs02800695_m1, Thermo Fisher Scientific Inc.) recognizing α-1-microglobulin/bikunin precursor mRNA, WAP four-disulfide core domain protein 2 mRNA, and hypoxanthine phosphoribosyltransferase 1. The expressions of α-1-microglobulin/bikunin precursor mRNA and WAP four-disulfide core domain protein 2 mRNA in each of the cell lines were compared by standardizing by the expression of hypoxanthine phosphoribosyltransferase 1 mRNA. In this experiment, Ad-1, MKN-45, KatoIII, and MCF7 were found in which the expression of α-1-microglobulin/bikunin precursor mRNA was 4 times or more higher than that of the normal human airway epithelial cell line (FIG. 9). Further, Ad-1, MKN-45, KatoIII, T3M4, and MCF7 were found in which the expression of WAP four-disulfide core domain protein2 mRNA was 4 times or more higher than that of the normal human airway epithelial cell line (FIG. 10).

The invention claimed is:

1. A lung adenocarcinoma detection method comprising a step of detecting in vitro a presence or an increase in a relative amount of at least one fragment selected from the group consisting of the following, in a test subject-derived sample:
   (p) a protein fragment having a C-terminal amino acid sequence of EGSCPQVNINFPQLG (SEQ ID NO: 23);
   (s) a protein fragment having a C-terminal amino acid sequence of EGSCPQVNIN (SEQ ID NO: 26); and
   with the use of at least one method selected from the group consisting of a mass spectrometric measurement method, an immunochemical measurement method, and a chromatography method.

2. The lung adenocarcinoma detection method according to claim 1, wherein the test subject-derived sample is urine.

3. The lung adenocarcinoma detection method according to claim 1, wherein
   the presence or an increase in a relative amount of the at least one protein fragment is determined by a fragmentation rate, and
   the fragmentation rate is a value expressed by protein fragmentation rate $(F_n) = C_n/I_n$,
   in which $C_n$ is an amount of the protein fragment, and $I_n$ is an amount of the protein from which the protein fragment is derived.

4. The lung adenocarcinoma detection method according to claim 1, wherein
   the presence or an increase in a relative amount of the protein fragment is determined by a relative ratio of the fragmentation rate of the protein derived from the test subject to the fragmentation rate of a protein from a healthy individual, the relative ratio being expressed by relative ratio ($R_n$) of protein fragmentation rates between the test subject and healthy individual $= F_p/F_h$,
   in which $F_p$ is a protein fragmentation rate in a test subject, and $F_h$ is an average value of protein fragmentation rates of healthy individual group, and
   the protein fragment is judged to be present or increased when the relative ratio is greater than 1.

5. The method of claim 1, wherein the at least one fragment is the protein fragment having a C-terminal amino acid sequence of EGSCPQVNIN (SEQ ID NO: 26).

6. The method of claim 1, wherein the at least one fragment is the protein fragment consisting of EGSCPQVNIN (SEQ ID NO: 26).

* * * * *

SEQUENCE LISTING

```
<160> NUMBER OF SEQ ID NOS: 35

<210> SEQ ID NO 1
<211> LENGTH: 418
<212> TYPE: PRT
<213> ORGANISM: Homo sapiens

<400> SEQUENCE: 1

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140
```

```
Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
            165                 170                 175

Ala Lys Lys Gln Ile Asn Asp Tyr Val Glu Lys Gly Thr Gln Gly Lys
        180                 185                 190

Ile Val Asp Leu Val Lys Glu Leu Asp Arg Asp Thr Val Phe Ala Leu
    195                 200                 205

Val Asn Tyr Ile Phe Phe Lys Gly Lys Trp Glu Arg Pro Phe Glu Val
210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 2
<211> LENGTH: 352
<212> TYPE: PRT
<213> ORGANISM: Homo sapiens

<400> SEQUENCE: 2

Met Arg Ser Leu Gly Ala Leu Leu Leu Leu Ser Ala Cys Leu Ala
1               5                   10                  15

Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
        35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95
```

```
Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
            115                 120                 125

Glu Tyr Ala Ile Phe Leu Thr Lys Lys Phe Ser Arg His His Gly Pro
            130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
                180                 185                 190

Gln Glu Pro Glu Pro Ile Leu Ile Pro Arg Val Arg Arg Ala Val Leu
            195                 200                 205

Pro Gln Glu Glu Glu Gly Ser Gly Gly Gly Gln Leu Val Thr Glu Val
            210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
            275                 280                 285

Leu Pro Ile Val Arg Gly Pro Cys Arg Ala Phe Ile Gln Leu Trp Ala
            290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Cys Arg Glu Tyr
                325                 330                 335

Cys Gly Val Pro Gly Asp Gly Asp Glu Glu Leu Leu Arg Phe Ser Asn
            340                 345                 350

<210> SEQ ID NO 3
<211> LENGTH: 128
<212> TYPE: PRT
<213> ORGANISM: Homo sapiens

<400> SEQUENCE: 3

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
                20                  25                  30

Asn Pro Thr Ala Asp Cys Lys Thr Ala Val Asn Cys Ser Ser Asp Phe
            35                  40                  45

Asp Ala Cys Leu Ile Thr Lys Ala Gly Leu Gln Val Tyr Asn Lys Cys
                50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Glu Lys Thr Val
            100                 105                 110

Leu Leu Leu Val Thr Pro Phe Leu Ala Ala Ala Trp Ser Leu His Pro
            115                 120                 125
```

<210> SEQ ID NO 4
<211> LENGTH: 2386
<212> TYPE: PRT
<213> ORGANISM: Homo sapiens

<400> SEQUENCE: 4

Met Leu Arg Gly Pro Gly Pro Gly Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu

```
              370                 375                 380
Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
                450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
                515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
                595                 600                 605

Ser Gly Pro Val Glu Val Phe Ile Thr Glu Thr Pro Ser Gln Pro Asn
                610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
                675                 680                 685

His Gln Glu Val Thr Arg Phe Asp Phe Thr Thr Thr Ser Thr Ser Thr
                690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
                770                 775                 780

Lys Tyr Ile Val Asn Val Tyr Gln Ile Ser Glu Asp Gly Glu Gln Ser
785                 790                 795                 800
```

-continued

```
Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
        850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
        930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080

Thr Leu Gln Pro Gly Ser Ser Ile Pro Pro Tyr Asn Thr Glu Val
    1085                1090                1095

Thr Glu Thr Thr Ile Val Ile Thr Trp Thr Pro Ala Pro Arg Ile
    1100                1105                1110

Gly Phe Lys Leu Gly Val Arg Pro Ser Gln Gly Gly Glu Ala Pro
    1115                1120                1125

Arg Glu Val Thr Ser Asp Ser Gly Ser Ile Val Val Ser Gly Leu
    1130                1135                1140

Thr Pro Gly Val Glu Tyr Val Tyr Thr Ile Gln Val Leu Arg Asp
    1145                1150                1155

Gly Gln Glu Arg Asp Ala Pro Ile Val Asn Lys Val Val Thr Pro
    1160                1165                1170

Leu Ser Pro Pro Thr Asn Leu His Leu Glu Ala Asn Pro Asp Thr
    1175                1180                1185

Gly Val Leu Thr Val Ser Trp Glu Arg Ser Thr Thr Pro Asp Ile
    1190                1195                1200
```

```
Thr Gly Tyr Arg Ile Thr Thr Thr Pro Thr Asn Gly Gln Gln Gly
1205                1210                1215

Asn Ser Leu Glu Glu Val Val His Ala Asp Gln Ser Ser Cys Thr
1220                1225                1230

Phe Asp Asn Leu Ser Pro Gly Leu Glu Tyr Asn Val Ser Val Tyr
1235                1240                1245

Thr Val Lys Asp Asp Lys Glu Ser Val Pro Ile Ser Asp Thr Ile
1250                1255                1260

Ile Pro Ala Val Pro Pro Thr Asp Leu Arg Phe Thr Asn Ile
1265                1270                1275

Gly Pro Asp Thr Met Arg Val Thr Trp Ala Pro Pro Ser Ile
1280                1285                1290

Asp Leu Thr Asn Phe Leu Val Arg Tyr Ser Pro Val Lys Asn Glu
1295                1300                1305

Glu Asp Val Ala Glu Leu Ser Ile Ser Pro Ser Asp Asn Ala Val
1310                1315                1320

Val Leu Thr Asn Leu Leu Pro Gly Thr Glu Tyr Val Val Ser Val
1325                1330                1335

Ser Ser Val Tyr Glu Gln His Glu Ser Thr Pro Leu Arg Gly Arg
1340                1345                1350

Gln Lys Thr Gly Leu Asp Ser Pro Thr Gly Ile Asp Phe Ser Asp
1355                1360                1365

Ile Thr Ala Asn Ser Phe Thr Val His Trp Ile Ala Pro Arg Ala
1370                1375                1380

Thr Ile Thr Gly Tyr Arg Ile Arg His His Pro Glu His Phe Ser
1385                1390                1395

Gly Arg Pro Arg Glu Asp Arg Val Pro His Ser Arg Asn Ser Ile
1400                1405                1410

Thr Leu Thr Asn Leu Thr Pro Gly Thr Glu Tyr Val Val Ser Ile
1415                1420                1425

Val Ala Leu Asn Gly Arg Glu Glu Ser Pro Leu Leu Ile Gly Gln
1430                1435                1440

Gln Ser Thr Val Ser Asp Val Pro Arg Asp Leu Glu Val Val Ala
1445                1450                1455

Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
```

-continued

```
            1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
    1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr
    1730                1735                1740

Pro Pro Asn Val Gln Leu Thr Gly Tyr Arg Val Arg Val Thr Pro
    1745                1750                1755

Lys Glu Lys Thr Gly Pro Met Lys Glu Ile Asn Leu Ala Pro Asp
    1760                1765                1770

Ser Ser Ser Val Val Val Ser Gly Leu Met Val Ala Thr Lys Tyr
    1775                1780                1785

Glu Val Ser Val Tyr Ala Leu Lys Asp Thr Leu Thr Ser Arg Pro
    1790                1795                1800

Ala Gln Gly Val Val Thr Thr Leu Glu Asn Val Ser Pro Pro Arg
    1805                1810                1815

Arg Ala Arg Val Thr Asp Ala Thr Glu Thr Thr Ile Thr Ile Ser
    1820                1825                1830

Trp Arg Thr Lys Thr Glu Thr Ile Thr Gly Phe Gln Val Asp Ala
    1835                1840                1845

Val Pro Ala Asn Gly Gln Thr Pro Ile Gln Arg Thr Ile Lys Pro
    1850                1855                1860

Asp Val Arg Ser Tyr Thr Ile Thr Gly Leu Gln Pro Gly Thr Asp
    1865                1870                1875

Tyr Lys Ile Tyr Leu Tyr Thr Leu Asn Asp Asn Ala Arg Ser Ser
    1880                1885                1890

Pro Val Val Ile Asp Ala Ser Thr Ala Ile Asp Ala Pro Ser Asn
    1895                1900                1905

Leu Arg Phe Leu Ala Thr Thr Pro Asn Ser Leu Leu Val Ser Trp
    1910                1915                1920

Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu
    1970                1975                1980

Pro Leu Ile Gly Arg Lys Lys Thr Asp Glu Leu Pro Gln Leu Val
    1985                1990                1995
```

```
Thr Leu Pro His Pro Asn Leu His Gly Pro Glu Ile Leu Asp Val
    2000            2005                2010

Pro Ser Thr Val Gln Lys Thr Pro Phe Val Thr His Pro Gly Tyr
    2015            2020                2025

Asp Thr Gly Asn Gly Ile Gln Leu Pro Gly Thr Ser Gly Gln Gln
    2030            2035                2040

Pro Ser Val Gly Gln Gln Met Ile Phe Glu Glu His Gly Phe Arg
    2045            2050                2055

Arg Thr Thr Pro Pro Thr Thr Ala Thr Pro Ile Arg His Arg Pro
    2060            2065                2070

Arg Pro Tyr Pro Pro Asn Val Gly Glu Glu Ile Gln Ile Gly His
    2075            2080                2085

Ile Pro Arg Glu Asp Val Asp Tyr His Leu Tyr Pro His Gly Pro
    2090            2095                2100

Gly Leu Asn Pro Asn Ala Ser Thr Gly Gln Glu Ala Leu Ser Gln
    2105            2110                2115

Thr Thr Ile Ser Trp Ala Pro Phe Gln Asp Thr Ser Glu Tyr Ile
    2120            2125                2130

Ile Ser Cys His Pro Val Gly Thr Asp Glu Glu Pro Leu Gln Phe
    2135            2140                2145

Arg Val Pro Gly Thr Ser Thr Ser Ala Thr Leu Thr Gly Leu Thr
    2150            2155                2160

Arg Gly Ala Thr Tyr Asn Val Ile Val Glu Ala Leu Lys Asp Gln
    2165            2170                2175

Gln Arg His Lys Val Arg Glu Val Val Thr Val Gly Asn Ser
    2180            2185                2190

Val Asn Glu Gly Leu Asn Gln Pro Thr Asp Asp Ser Cys Phe Asp
    2195            2200                2205

Pro Tyr Thr Val Ser His Tyr Ala Val Gly Asp Glu Trp Glu Arg
    2210            2215                2220

Met Ser Glu Ser Gly Phe Lys Leu Leu Cys Gln Cys Leu Gly Phe
    2225            2230                2235

Gly Ser Gly His Phe Arg Cys Asp Ser Ser Arg Trp Cys His Asp
    2240            2245                2250

Asn Gly Val Asn Tyr Lys Ile Gly Glu Lys Trp Asp Arg Gln Gly
    2255            2260                2265

Glu Asn Gly Gln Met Met Ser Cys Thr Cys Leu Gly Asn Gly Lys
    2270            2275                2280

Gly Glu Phe Lys Cys Asp Pro His Glu Ala Thr Cys Tyr Asp Asp
    2285            2290                2295

Gly Lys Thr Tyr His Val Gly Glu Gln Trp Gln Lys Glu Tyr Leu
    2300            2305                2310

Gly Ala Ile Cys Ser Cys Thr Cys Phe Gly Gly Gln Arg Gly Trp
    2315            2320                2325

Arg Cys Asp Asn Cys Arg Arg Pro Gly Gly Glu Pro Ser Pro Glu
    2330            2335                2340

Gly Thr Thr Gly Gln Ser Tyr Asn Gln Tyr Ser Gln Arg Tyr His
    2345            2350                2355

Gln Arg Thr Asn Thr Asn Val Asn Cys Pro Ile Glu Cys Phe Met
    2360            2365                2370

Pro Leu Asp Val Gln Ala Asp Arg Glu Asp Ser Arg Glu
    2375            2380                2385
```

<210> SEQ ID NO 5
<211> LENGTH: 356
<212> TYPE: PRT
<213> ORGANISM: Homo sapiens

<400> SEQUENCE: 5

| | | | | | | | | | | | | | | | |
|---|---|---|---|---|---|---|---|---|---|---|---|---|---|---|---|
| Met | Ala | Ala | Glu | Gly | Trp | Ile | Trp | Arg | Trp | Gly | Trp | Gly | Arg | Arg | Cys |
| 1 | | | | 5 | | | | | 10 | | | | | 15 | |
| Leu | Gly | Arg | Pro | Gly | Leu | Leu | Gly | Pro | Gly | Pro | Gly | Pro | Thr | Thr | Pro |
| | | | 20 | | | | | 25 | | | | | 30 | | |
| Leu | Phe | Leu | Leu | Leu | Leu | Leu | Gly | Ser | Val | Thr | Ala | Asp | Ile | Thr | Asp |
| | | | 35 | | | | | 40 | | | | | 45 | | |
| Gly | Asn | Ser | Glu | His | Leu | Lys | Arg | Glu | His | Ser | Leu | Ile | Lys | Pro | Tyr |
| 50 | | | | | 55 | | | | | 60 | | | | | |
| Gln | Gly | Val | Gly | Ser | Ser | Met | Pro | Leu | Trp | Asp | Phe | Gln | Gly | Ser | |
| 65 | | | | 70 | | | | 75 | | | | | 80 | | |
| Thr | Met | Leu | Thr | Ser | Gln | Tyr | Val | Arg | Leu | Thr | Pro | Asp | Glu | Arg | Ser |
| | | | | 85 | | | | | 90 | | | | | 95 | |
| Lys | Glu | Gly | Ser | Ile | Trp | Asn | His | Gln | Pro | Cys | Phe | Leu | Lys | Asp | Trp |
| | | | 100 | | | | | 105 | | | | | 110 | | |
| Glu | Met | His | Val | His | Phe | Lys | Val | His | Gly | Thr | Gly | Lys | Lys | Asn | Leu |
| | | | 115 | | | | | 120 | | | | | 125 | | |
| His | Gly | Asp | Gly | Ile | Ala | Leu | Trp | Tyr | Thr | Arg | Asp | Arg | Leu | Val | Pro |
| | | 130 | | | | | 135 | | | | | 140 | | | |
| Gly | Pro | Val | Phe | Gly | Ser | Lys | Asp | Asn | Phe | His | Gly | Leu | Ala | Ile | Phe |
| 145 | | | | | 150 | | | | | 155 | | | | | 160 |
| Leu | Asp | Thr | Tyr | Pro | Asn | Asp | Glu | Thr | Thr | Glu | Arg | Val | Phe | Pro | Tyr |
| | | | | 165 | | | | | 170 | | | | | 175 | |
| Ile | Ser | Val | Met | Val | Asn | Asn | Gly | Ser | Leu | Ser | Tyr | Asp | His | Ser | Lys |
| | | | 180 | | | | | 185 | | | | | 190 | | |
| Asp | Gly | Arg | Trp | Thr | Glu | Leu | Ala | Gly | Cys | Thr | Ala | Asp | Phe | Arg | Asn |
| | | 195 | | | | | 200 | | | | | 205 | | | |
| Arg | Asp | His | Asp | Thr | Phe | Leu | Ala | Val | Arg | Tyr | Ser | Arg | Gly | Arg | Leu |
| | 210 | | | | | 215 | | | | | 220 | | | | |
| Thr | Val | Met | Thr | Asp | Leu | Glu | Asp | Lys | Asn | Glu | Trp | Lys | Asn | Cys | Ile |
| 225 | | | | | 230 | | | | | 235 | | | | | 240 |
| Asp | Ile | Thr | Gly | Val | Arg | Leu | Pro | Thr | Gly | Tyr | Tyr | Phe | Gly | Ala | Ser |
| | | | | 245 | | | | | 250 | | | | | 255 | |
| Ala | Gly | Thr | Gly | Asp | Leu | Ser | Asp | Asn | His | Asp | Ile | Ile | Ser | Met | Lys |
| | | | 260 | | | | | 265 | | | | | 270 | | |
| Leu | Phe | Gln | Leu | Met | Val | Glu | His | Thr | Pro | Asp | Glu | Glu | Ser | Ile | Asp |
| | | 275 | | | | | 280 | | | | | 285 | | | |
| Trp | Thr | Lys | Ile | Glu | Pro | Ser | Val | Asn | Phe | Leu | Lys | Ser | Pro | Lys | Asp |
| | 290 | | | | | 295 | | | | | 300 | | | | |
| Asn | Val | Asp | Asp | Pro | Thr | Gly | Asn | Phe | Arg | Ser | Gly | Pro | Leu | Thr | Gly |
| 305 | | | | | 310 | | | | | 315 | | | | | 320 |
| Trp | Arg | Val | Phe | Leu | Leu | Leu | Leu | Cys | Ala | Leu | Leu | Gly | Ile | Val | Val |
| | | | | 325 | | | | | 330 | | | | | 335 | |
| Cys | Ala | Val | Val | Gly | Ala | Val | Val | Phe | Gln | Lys | Arg | Gln | Glu | Arg | Asn |
| | | | 340 | | | | | 345 | | | | | 350 | | |
| Lys | Arg | Phe | Tyr | | | | | | | | | | | | |
| | | | 355 | | | | | | | | | | | | |

<210> SEQ ID NO 6

<211> LENGTH: 673
<212> TYPE: PRT
<213> ORGANISM: Homo sapiens

<400> SEQUENCE: 6

```
Met Cys Ser Arg Val Pro Leu Leu Pro Leu Leu Leu Leu Ala
1               5                   10                  15

Leu Gly Pro Gly Val Gln Gly Cys Pro Ser Gly Cys Gln Cys Ser Gln
                20                  25                  30

Pro Gln Thr Val Phe Cys Thr Ala Arg Gln Gly Thr Thr Val Pro Arg
            35                  40                  45

Asp Val Pro Pro Asp Thr Val Gly Leu Tyr Val Phe Glu Asn Gly Ile
50                  55                  60

Thr Met Leu Asp Ala Gly Ser Phe Ala Gly Leu Pro Gly Leu Gln Leu
65                  70                  75                  80

Leu Asp Leu Ser Gln Asn Gln Ile Ala Ser Leu Pro Ser Gly Val Phe
                85                  90                  95

Gln Pro Leu Ala Asn Leu Ser Asn Leu Asp Leu Thr Ala Asn Arg Leu
            100                 105                 110

His Glu Ile Thr Asn Glu Thr Phe Arg Gly Leu Arg Arg Leu Glu Arg
        115                 120                 125

Leu Tyr Leu Gly Lys Asn Arg Ile Arg His Ile Gln Pro Gly Ala Phe
    130                 135                 140

Asp Thr Leu Asp Arg Leu Leu Glu Leu Lys Leu Gln Asp Asn Glu Leu
145                 150                 155                 160

Arg Ala Leu Pro Pro Leu Arg Leu Pro Arg Leu Leu Leu Leu Asp Leu
                165                 170                 175

Ser His Asn Ser Leu Leu Ala Leu Glu Pro Gly Ile Leu Asp Thr Ala
            180                 185                 190

Asn Val Glu Ala Leu Arg Leu Ala Gly Leu Gly Leu Gln Gln Leu Asp
        195                 200                 205

Glu Gly Leu Phe Ser Arg Leu Arg Asn Leu His Asp Leu Asp Val Ser
    210                 215                 220

Asp Asn Gln Leu Glu Arg Val Pro Pro Val Ile Arg Gly Leu Arg Gly
225                 230                 235                 240

Leu Thr Arg Leu Arg Leu Ala Gly Asn Thr Arg Ile Ala Gln Leu Arg
                245                 250                 255

Pro Glu Asp Leu Ala Gly Leu Ala Ala Leu Gln Glu Leu Asp Val Ser
            260                 265                 270

Asn Leu Ser Leu Gln Ala Leu Pro Gly Asp Leu Ser Gly Leu Phe Pro
        275                 280                 285

Arg Leu Arg Leu Leu Ala Ala Ala Arg Asn Pro Phe Asn Cys Val Cys
    290                 295                 300

Pro Leu Ser Trp Phe Gly Pro Trp Val Arg Glu Ser His Val Thr Leu
305                 310                 315                 320

Ala Ser Pro Glu Glu Thr Arg Cys His Phe Pro Pro Lys Asn Ala Gly
                325                 330                 335

Arg Leu Leu Leu Glu Leu Asp Tyr Ala Asp Phe Gly Cys Pro Ala Thr
            340                 345                 350

Thr Thr Thr Ala Thr Val Pro Thr Arg Pro Val Val Arg Glu Pro
        355                 360                 365

Thr Ala Leu Ser Ser Leu Ala Pro Thr Trp Leu Ser Pro Thr Glu
    370                 375                 380

Pro Ala Thr Glu Ala Pro Ser Pro Pro Ser Thr Ala Pro Pro Thr Val
```

-continued

```
             385                 390                 395                 400
Gly Pro Val Pro Gln Pro Gln Asp Cys Pro Ser Thr Cys Leu Asn
                405                 410                 415

Gly Gly Thr Cys His Leu Gly Thr Arg His Leu Ala Cys Leu Cys
                420                 425                 430

Pro Glu Gly Phe Thr Gly Leu Tyr Cys Glu Ser Gln Met Gly Gln Gly
                435                 440                 445

Thr Arg Pro Ser Pro Thr Pro Val Thr Pro Arg Pro Arg Ser Leu
450                 455                 460

Thr Leu Gly Ile Glu Pro Val Ser Pro Thr Ser Leu Arg Val Gly Leu
465                 470                 475                 480

Gln Arg Tyr Leu Gln Gly Ser Ser Val Gln Leu Arg Ser Leu Arg Leu
                485                 490                 495

Thr Tyr Arg Asn Leu Ser Gly Pro Asp Lys Arg Leu Val Thr Leu Arg
                500                 505                 510

Leu Pro Ala Ser Leu Ala Glu Tyr Thr Val Thr Gln Leu Arg Pro Asn
                515                 520                 525

Ala Thr Tyr Ser Val Cys Val Met Pro Leu Gly Pro Gly Arg Val Pro
530                 535                 540

Glu Gly Glu Glu Ala Cys Gly Glu Ala His Thr Pro Pro Ala Val His
545                 550                 555                 560

Ser Asn His Ala Pro Val Thr Gln Ala Arg Glu Gly Asn Leu Pro Leu
                565                 570                 575

Leu Ile Ala Pro Ala Leu Ala Ala Val Leu Leu Ala Ala Leu Ala Ala
                580                 585                 590

Val Gly Ala Ala Tyr Cys Val Arg Arg Gly Arg Ala Met Ala Ala Ala
                595                 600                 605

Ala Gln Asp Lys Gly Gln Val Gly Pro Gly Ala Gly Pro Leu Glu Leu
                610                 615                 620

Glu Gly Val Lys Val Pro Leu Glu Pro Gly Pro Lys Ala Thr Glu Gly
625                 630                 635                 640

Gly Gly Glu Ala Leu Pro Ser Gly Ser Glu Cys Glu Val Pro Leu Met
                645                 650                 655

Gly Phe Pro Gly Pro Gly Leu Gln Ser Pro Leu His Ala Lys Pro Tyr
                660                 665                 670

Ile

<210> SEQ ID NO 7
<211> LENGTH: 124
<212> TYPE: PRT
<213> ORGANISM: Homo sapiens

<400> SEQUENCE: 7

Met Pro Ala Cys Arg Leu Gly Pro Leu Ala Ala Ala Leu Leu Leu Ser
1               5                   10                  15

Leu Leu Leu Phe Gly Phe Thr Leu Val Ser Gly Thr Gly Ala Glu Lys
                20                  25                  30

Thr Gly Val Cys Pro Glu Leu Gln Ala Asp Gln Asn Cys Thr Gln Glu
            35                  40                  45

Cys Val Ser Asp Ser Glu Cys Ala Asp Asn Leu Lys Cys Cys Ser Ala
        50                  55                  60

Gly Cys Ala Thr Phe Cys Ser Leu Pro Asn Asp Lys Glu Gly Ser Cys
65                  70                  75                  80

Pro Gln Val Asn Ile Asn Phe Pro Gln Leu Gly Leu Cys Arg Asp Gln
```

-continued

```
                            85                  90                  95
Cys Gln Val Asp Ser Gln Cys Pro Gly Gln Met Lys Cys Cys Arg Asn
                100                 105                 110
Gly Cys Gly Lys Val Ser Cys Val Thr Pro Asn Phe
            115                 120

<210> SEQ ID NO 8
<211> LENGTH: 443
<212> TYPE: PRT
<213> ORGANISM: Homo sapiens

<400> SEQUENCE: 8

Met Asp Phe Pro Cys Leu Trp Leu Gly Leu Leu Leu Pro Leu Val Ala
1               5                   10                  15

Ala Leu Asp Phe Asn Tyr His Arg Gln Glu Gly Met Glu Ala Phe Leu
            20                  25                  30

Lys Thr Val Ala Gln Asn Tyr Ser Ser Val Thr His Leu His Ser Ile
        35                  40                  45

Gly Lys Ser Val Lys Gly Arg Asn Leu Trp Val Leu Val Val Gly Arg
    50                  55                  60

Phe Pro Lys Glu His Arg Ile Gly Ile Pro Glu Phe Lys Tyr Val Ala
65                  70                  75                  80

Asn Met His Gly Asp Glu Thr Val Gly Arg Glu Leu Leu Leu His Leu
                85                  90                  95

Ile Asp Tyr Leu Val Thr Ser Asp Gly Lys Asp Pro Glu Ile Thr Asn
            100                 105                 110

Leu Ile Asn Ser Thr Arg Ile His Ile Met Pro Ser Met Asn Pro Asp
        115                 120                 125

Gly Phe Glu Ala Val Lys Lys Pro Asp Cys Tyr Tyr Ser Ile Gly Arg
    130                 135                 140

Glu Asn Tyr Asn Gln Tyr Asp Leu Asn Arg Asn Phe Pro Asp Ala Phe
145                 150                 155                 160

Glu Tyr Asn Asn Val Ser Arg Gln Pro Glu Thr Val Ala Val Met Lys
                165                 170                 175

Trp Leu Lys Thr Glu Thr Phe Val Leu Ser Ala Asn Leu His Gly Gly
            180                 185                 190

Ala Leu Val Ala Ser Tyr Pro Phe Asp Asn Gly Val Gln Ala Thr Gly
        195                 200                 205

Ala Leu Tyr Ser Arg Ser Leu Thr Pro Asp Asp Val Phe Gln Tyr
    210                 215                 220

Leu Ala His Thr Tyr Ala Ser Arg Asn Pro Asn Met Lys Lys Gly Asp
225                 230                 235                 240

Glu Cys Lys Asn Lys Met Asn Phe Pro Asn Gly Val Thr Asn Gly Tyr
                245                 250                 255

Ser Trp Tyr Pro Leu Gln Gly Gly Met Gln Asp Tyr Asn Tyr Ile Trp
            260                 265                 270

Ala Gln Cys Phe Glu Ile Thr Leu Glu Leu Ser Cys Cys Lys Tyr Pro
        275                 280                 285

Arg Glu Glu Lys Leu Pro Ser Phe Trp Asn Asn Lys Ala Ser Leu
    290                 295                 300

Ile Glu Tyr Ile Lys Gln Val His Leu Gly Val Lys Gly Gln Val Phe
305                 310                 315                 320

Asp Gln Asn Gly Asn Pro Leu Pro Asn Val Ile Val Glu Val Gln Asp
                325                 330                 335
```

```
Arg Lys His Ile Cys Pro Tyr Arg Thr Asn Lys Tyr Gly Glu Tyr Tyr
            340                 345                 350

Leu Leu Leu Leu Pro Gly Ser Tyr Ile Ile Asn Val Thr Val Pro Gly
            355                 360                 365

His Asp Pro His Ile Thr Lys Val Ile Ile Pro Glu Lys Ser Gln Asn
            370                 375                 380

Phe Ser Ala Leu Lys Lys Asp Ile Leu Leu Pro Phe Gln Gly Gln Leu
385                 390                 395                 400

Asp Ser Ile Pro Val Ser Asn Pro Ser Cys Pro Met Ile Pro Leu Tyr
            405                 410                 415

Arg Asn Leu Pro Asp His Ser Ala Ala Thr Lys Pro Ser Leu Phe Leu
            420                 425                 430

Phe Leu Val Ser Leu Leu His Ile Phe Phe Lys
            435                 440

<210> SEQ ID NO 9
<211> LENGTH: 282
<212> TYPE: PRT
<213> ORGANISM: Homo sapiens

<400> SEQUENCE: 9

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
            35                  40                  45

Gln Ile Leu Ser Arg Tyr Asp Ile Ala Leu Val Gln Glu Val Arg Asp
    50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Gly Cys Glu Pro Cys Gly Asn
            115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270
```

```
Asp His Tyr Pro Val Glu Val Met Leu Lys
        275                 280

<210> SEQ ID NO 10
<211> LENGTH: 250
<212> TYPE: PRT
<213> ORGANISM: Homo sapiens

<400> SEQUENCE: 10

Met Arg Gly Thr Pro Lys Thr His Leu Leu Ala Phe Ser Leu Leu Cys
1               5                   10                  15

Leu Leu Ser Lys Val Arg Thr Gln Leu Cys Pro Thr Pro Cys Thr Cys
            20                  25                  30

Pro Trp Pro Pro Pro Arg Cys Pro Leu Gly Val Pro Leu Val Leu Asp
        35                  40                  45

Gly Cys Gly Cys Cys Arg Val Cys Ala Arg Arg Leu Gly Glu Pro Cys
    50                  55                  60

Asp Gln Leu His Val Cys Asp Ala Ser Gln Gly Leu Val Cys Gln Pro
65                  70                  75                  80

Gly Ala Gly Pro Gly Gly Arg Gly Ala Leu Cys Leu Leu Ala Glu Asp
                85                  90                  95

Asp Ser Ser Cys Glu Val Asn Gly Arg Leu Tyr Arg Glu Gly Glu Thr
            100                 105                 110

Phe Gln Pro His Cys Ser Ile Arg Cys Arg Cys Glu Asp Gly Gly Phe
        115                 120                 125

Thr Cys Val Pro Leu Cys Ser Glu Asp Val Arg Leu Pro Ser Trp Asp
    130                 135                 140

Cys Pro His Pro Arg Arg Val Glu Val Leu Gly Lys Cys Cys Pro Glu
145                 150                 155                 160

Trp Val Cys Gly Gln Gly Gly Gly Leu Gly Thr Gln Pro Leu Pro Ala
                165                 170                 175

Gln Gly Pro Gln Phe Ser Gly Leu Val Ser Ser Leu Pro Pro Gly Val
            180                 185                 190

Pro Cys Pro Glu Trp Ser Thr Ala Trp Gly Pro Cys Ser Thr Thr Cys
        195                 200                 205

Gly Leu Gly Met Ala Thr Arg Val Ser Asn Gln Asn Arg Phe Cys Arg
    210                 215                 220

Leu Glu Thr Gln Arg Arg Leu Cys Leu Ser Arg Pro Cys Pro Pro Ser
225                 230                 235                 240

Arg Gly Arg Ser Pro Gln Asn Ser Ala Phe
                245                 250

<210> SEQ ID NO 11
<211> LENGTH: 9
<212> TYPE: PRT
<213> ORGANISM: Homo sapiens

<400> SEQUENCE: 11

Gly Thr Glu Ala Ala Gly Ala Met Phe
1               5

<210> SEQ ID NO 12
<211> LENGTH: 8
<212> TYPE: PRT
<213> ORGANISM: Homo sapiens

<400> SEQUENCE: 12
```

Cys Val Leu Phe Pro Tyr Gly Gly
1               5

<210> SEQ ID NO 13
<211> LENGTH: 7
<212> TYPE: PRT
<213> ORGANISM: Homo sapiens

<400> SEQUENCE: 13

Glu Tyr Cys Gly Val Pro Gly
1               5

<210> SEQ ID NO 14
<211> LENGTH: 9
<212> TYPE: PRT
<213> ORGANISM: Homo sapiens

<400> SEQUENCE: 14

Glu Tyr Cys Gly Val Pro Gly Asp Gly
1               5

<210> SEQ ID NO 15
<211> LENGTH: 11
<212> TYPE: PRT
<213> ORGANISM: Homo sapiens

<400> SEQUENCE: 15

Glu Tyr Cys Gly Val Pro Gly Asp Gly Asp Glu
1               5                   10

<210> SEQ ID NO 16
<211> LENGTH: 12
<212> TYPE: PRT
<213> ORGANISM: Homo sapiens

<400> SEQUENCE: 16

Glu Tyr Cys Gly Val Pro Gly Asp Gly Asp Glu Glu
1               5                   10

<210> SEQ ID NO 17
<211> LENGTH: 13
<212> TYPE: PRT
<213> ORGANISM: Homo sapiens

<400> SEQUENCE: 17

Glu Tyr Cys Gly Val Pro Gly Asp Gly Asp Glu Glu Leu
1               5                   10

<210> SEQ ID NO 18
<211> LENGTH: 14
<212> TYPE: PRT
<213> ORGANISM: Homo sapiens

<400> SEQUENCE: 18

Glu Tyr Cys Gly Val Pro Gly Asp Gly Asp Glu Glu Leu Leu
1               5                   10

<210> SEQ ID NO 19
<211> LENGTH: 12
<212> TYPE: PRT
<213> ORGANISM: Homo sapiens

<400> SEQUENCE: 19

Gly Glu Cys Val Pro Gly Glu Gln Glu Pro Glu Pro
1               5                   10

<210> SEQ ID NO 20
<211> LENGTH: 16
<212> TYPE: PRT
<213> ORGANISM: Homo sapiens

<400> SEQUENCE: 20

Gly Glu Cys Val Pro Gly Glu Gln Glu Pro Glu Pro Ile Leu Ile Pro
1               5                   10                  15

<210> SEQ ID NO 21
<211> LENGTH: 9
<212> TYPE: PRT
<213> ORGANISM: Homo sapiens

<400> SEQUENCE: 21

Asp Leu Cys Asn Phe Asn Glu Gln Leu
1               5

<210> SEQ ID NO 22
<211> LENGTH: 7
<212> TYPE: PRT
<213> ORGANISM: Homo sapiens

<400> SEQUENCE: 22

Phe Gly Phe Cys Pro Met Ala
1               5

<210> SEQ ID NO 23
<211> LENGTH: 15
<212> TYPE: PRT
<213> ORGANISM: Homo sapiens

<400> SEQUENCE: 23

Glu Gly Ser Cys Pro Gln Val Asn Ile Asn Phe Pro Gln Leu Gly
1               5                   10                  15

<210> SEQ ID NO 24
<211> LENGTH: 6
<212> TYPE: PRT
<213> ORGANISM: Homo sapiens

<400> SEQUENCE: 24

Leu Pro Thr Gly Tyr Tyr
1               5

<210> SEQ ID NO 25
<211> LENGTH: 9
<212> TYPE: PRT
<213> ORGANISM: Homo sapiens

<400> SEQUENCE: 25

Tyr Leu Gln Gly Ser Ser Val Gln Leu
1               5

<210> SEQ ID NO 26
<211> LENGTH: 10
<212> TYPE: PRT
<213> ORGANISM: Homo sapiens

<400> SEQUENCE: 26

Glu Gly Ser Cys Pro Gln Val Asn Ile Asn
1               5                   10

```
<210> SEQ ID NO 27
<211> LENGTH: 9
<212> TYPE: PRT
<213> ORGANISM: Homo sapiens

<400> SEQUENCE: 27

Glu Asn Tyr Asn Gln Tyr Asp Leu Asn
1               5

<210> SEQ ID NO 28
<211> LENGTH: 17
<212> TYPE: PRT
<213> ORGANISM: Homo sapiens

<400> SEQUENCE: 28

Gly Ala Val Val Pro Asp Ser Ala Leu Pro Phe Asn Phe Gln Ala Ala
1               5                   10                  15

Tyr

<210> SEQ ID NO 29
<211> LENGTH: 16
<212> TYPE: PRT
<213> ORGANISM: Homo sapiens

<400> SEQUENCE: 29

Glu Gly Ser Cys Pro Gln Val Asn Ile Asn Phe Pro Gln Leu Gly Leu
1               5                   10                  15

<210> SEQ ID NO 30
<211> LENGTH: 11
<212> TYPE: PRT
<213> ORGANISM: Homo sapiens

<400> SEQUENCE: 30

Gly Ala Leu Cys Leu Leu Ala Glu Asp Asp Ser
1               5                   10

<210> SEQ ID NO 31
<211> LENGTH: 8
<212> TYPE: PRT
<213> ORGANISM: Homo sapiens

<400> SEQUENCE: 31

Glu Tyr Cys Gly Val Pro Gly Asp
1               5

<210> SEQ ID NO 32
<211> LENGTH: 11
<212> TYPE: PRT
<213> ORGANISM: Homo sapiens

<400> SEQUENCE: 32

Gly Glu Cys Val Pro Gly Glu Gln Glu Pro Glu
1               5                   10

<210> SEQ ID NO 33
<211> LENGTH: 12
<212> TYPE: PRT
<213> ORGANISM: Homo sapiens

<400> SEQUENCE: 33

Glu Tyr Cys Gly Val Pro Gly Asp Asp Glu Glu Leu
1               5                   10
```

```
<210> SEQ ID NO 34
<211> LENGTH: 14
<212> TYPE: PRT
<213> ORGANISM: Homo sapiens

<400> SEQUENCE: 34

Glu Gly Ser Cys Pro Gln Val Asn Asn Phe Pro Gln Leu Gly
1               5                   10

<210> SEQ ID NO 35
<211> LENGTH: 4
<212> TYPE: PRT
<213> ORGANISM: Homo sapiens

<400> SEQUENCE: 35

Arg Phe Ser Asn
1
```